US012778489B2

(12) United States Patent
Evans

(10) Patent No.: US 12,778,489 B2
(45) Date of Patent: Nov. 3, 2026

(54) METHOD AND APPARATUS FOR REDUCING THE RISK OF NEONATAL NEUROLOGICAL INJURY

(71) Applicant: Mark Evans, Las Vegas, NV (US)

(72) Inventor: Mark Evans, Las Vegas, NV (US)

(73) Assignee: Mark Evans, Las Vegas, NV (US)

( * ) Notice: Subject to any disclaimer, the term of this patent is extended or adjusted under 35 U.S.C. 154(b) by 630 days.

(21) Appl. No.: 17/294,038

(22) PCT Filed: Nov. 14, 2019

(86) PCT No.: PCT/US2019/061465
§ 371 (c)(1),
(2) Date: May 14, 2021

(87) PCT Pub. No.: WO2020/102524
PCT Pub. Date: May 22, 2020

(65) Prior Publication Data

US 2022/0007999 A1 Jan. 13, 2022

Related U.S. Application Data

(60) Provisional application No. 62/791,337, filed on Jan. 11, 2019, provisional application No. 62/767,147, filed on Nov. 14, 2018.

(51) Int. Cl.
*A61B 5/00* (2006.01)
*A61B 5/024* (2006.01)

(52) U.S. Cl.
CPC ........ *A61B 5/4362* (2013.01); *A61B 5/02405* (2013.01); *A61B 5/02411* (2013.01); *A61B 5/7275* (2013.01)

(58) Field of Classification Search
CPC .............. A61B 5/4362; A61B 5/02405; A61B 5/02411; A61B 5/7275

(Continued)

(56) References Cited

U.S. PATENT DOCUMENTS 3,989,034 A 11/1976 Hojaiban
4,821,732 A 4/1989 Lippes
(Continued)

FOREIGN PATENT DOCUMENTS

CN 1631322 A 6/2005
CN 101010032 A 8/2007
(Continued)

OTHER PUBLICATIONS

The Apgar score. Committee Opinion No. 644. American College of Obstetricians and Gynecologists. Obstet Gynecol 2015; 126: e52-5. (Year: 2015).*

(Continued)

*Primary Examiner* — Michael T. Holtzclaw
(74) *Attorney, Agent, or Firm* — Dickinson Wright PLLC

(57) ABSTRACT

An apparatus and method involves monitoring in a pregnant patient during labor a first set of parameters indicative of a present level of risk for neurological injury to the fetus and determining prior to delivery and/or during the first approximately 5 minutes following delivery a present level of risk for neurological injury based on the first set of parameters at a point in time during labor just prior to delivery. The determined risk corresponds to one of a plurality of predetermined levels of predicted risk for neurological injury to the neonate. The apparatus can indicate via an output the determined level of risk and/or the corresponding predetermined level of predicted risk, and information representing the received input signals corresponding to the one or more postnatal parameters.

8 Claims, 19 Drawing Sheets

(58) Field of Classification Search
USPC .......................................................... 600/511
See application file for complete search history.

(56) References Cited

U.S. PATENT DOCUMENTS

| | | | |
|---|---|---|---|
| 4,951,680 A | 8/1990 | Kirk | |
| 5,069,218 A | 12/1991 | Ikeda | |
| 5,088,497 A | 2/1992 | Ikeda | |
| 5,123,420 A | 6/1992 | Paret | |
| 5,425,362 A | 6/1995 | Siker | |
| 5,433,204 A | 7/1995 | Olson | |
| 5,442,940 A | 8/1995 | Secker | |
| 5,474,065 A | 12/1995 | Meathrel | |
| 5,497,317 A | 3/1996 | Hawkins | |
| 5,511,553 A | 4/1996 | Segalowitz | |
| 5,596,993 A | 1/1997 | Oriol | |
| 5,623,939 A | 4/1997 | Garfield | |
| 5,808,609 A * | 9/1998 | Guha .................... | G06T 11/206 715/848 |
| 5,851,188 A | 12/1998 | Bullard | |
| 5,954,663 A | 9/1999 | Gat | |
| 5,957,855 A | 9/1999 | Oriol | |
| 6,024,701 A | 2/2000 | Almog | |
| 6,254,537 B1 | 7/2001 | Nguyen | |
| 6,340,346 B1 | 1/2002 | Almog | |
| 6,423,016 B1 | 7/2002 | Hamilton | |
| 6,434,418 B1 | 8/2002 | Neal et al. | |
| 6,453,183 B1 * | 9/2002 | Walker ............... | A61B 5/14553 600/338 |
| 6,522,916 B1 | 2/2003 | Kwon | |
| 6,751,498 B1 | 6/2004 | Greenberg | |
| 7,113,819 B2 | 9/2006 | Hamilton | |
| 7,313,424 B2 | 12/2007 | Mayevsky | |
| 7,314,451 B2 | 1/2008 | Halperin | |
| 7,333,850 B2 | 2/2008 | Marossero | |
| 7,850,625 B2 | 12/2010 | Paltieli | |
| 9,131,860 B2 | 9/2015 | Evans | |
| 9,591,983 B2 | 3/2017 | Amir | |
| 10,448,891 B2 | 10/2019 | Amir | |
| 11,045,148 B2 * | 6/2021 | Roberts ................ | A61B 5/4362 |
| 2002/0193670 A1 * | 12/2002 | Garfield ................. | A61B 5/344 600/304 |
| 2003/0187364 A1 | 10/2003 | Hamilton | |
| 2004/0082842 A1 | 4/2004 | Lumba | |
| 2004/0100376 A1 | 5/2004 | Lye | |
| 2005/0267377 A1 | 12/2005 | Marossero | |
| 2006/0074329 A1 | 4/2006 | Ferguson, II | |
| 2007/0213627 A1 | 9/2007 | James | |
| 2007/0233203 A1 | 10/2007 | Euliano | |
| 2007/0255588 A1 | 11/2007 | Hamilton | |
| 2010/0168528 A1 | 7/2010 | Evans | |
| 2010/0268124 A1 | 10/2010 | Hamilton | |
| 2011/0071414 A1 | 3/2011 | Heil | |
| 2012/0130200 A1 * | 5/2012 | Cipriano .................. | A61B 5/08 600/301 |
| 2012/0142604 A1 | 6/2012 | Faivre | |
| 2013/0137998 A1 * | 5/2013 | Lange .................... | G16H 50/30 600/587 |
| 2013/0281861 A1 | 10/2013 | Flomerfelt | |
| 2014/0301949 A1 | 10/2014 | Rabi | |
| 2015/0051115 A1 | 2/2015 | Everett | |
| 2015/0157276 A1 | 6/2015 | Gratacos | |
| 2016/0270658 A1 * | 9/2016 | Ater ..................... | A61B 8/0866 |
| 2017/0308662 A1 | 10/2017 | Hamilton | |
| 2017/0355754 A1 * | 12/2017 | Watzlawik ....... | A61K 39/39533 |

FOREIGN PATENT DOCUMENTS

| | | |
|---|---|---|
| EP | 0384339 | 4/1997 |
| EP | 1568316 | 8/2008 |
| JP | 2012524627 | 10/2012 |
| JP | 2013545087 | 12/2013 |
| KR | 20010105460 | 11/2001 |
| WO | 9849942 | 11/1998 |
| WO | 0001117 | 1/2000 |
| WO | 2007120873 | 10/2007 |
| WO | 2012051519 | 4/2012 |
| WO | 2018094398 | 5/2018 |

OTHER PUBLICATIONS

Macones, et al. The 2008 National Institute of Child Health and Human Development Workshop Report on Electronic Fetal Monitoring: Update on Definitions, Interpretation, and Research Guidelines. Obstetrics & Gynecology 112(3):p. 661-666, Sep. 2008. | DOI: 10.1097/AOG.0b013e3181841395 (Year: 2008).*

Higgins, Umbilical-cord blood gas analysis, Oct. 2014, Radiometer Medical ApS (Year: 2014).*

"What Are the Stages of Labor?" Sep. 1, 2017. Eunice Kennedy Shriver National Institute of Child Health and Human Development, U.S. Department of Health and Human Services. (Year: 2017).*

Intermittent Auscultation for Intrapartum Fetal Heart Rate Surveillance; Journal of Midwifery & Women's Health; March J010; No. 11; pp. 397-403; Elsevier Inc; Silver Spring, MD.

Parer et al., A framework for standardized management of intrapartum fetal heart rate patterns, Am. Jour. Obst. & Gyn., Jul. 2007, pp. 26.e1-26.e6.

Parer, JT, FHR Monitoring: Can we expect improvements soon?, Maternal Fetal Medicine, University of California San Francisco, MFM Fellows Videoconference Series, May 21, 2008.

Yuki Kodama et al., Intrapartum fetal heart rate patterns in infants with (>-34 weeks) with poor neurological outcome; Early Human Development 85 (2009), pp. 235-238.

Deidre M. Murray, M.D., et al., Fetal Heart Rate Patterns in Neonatal Hypoxic-Ischemic Encephalopathy: Relationship with Early Cerebral Activity and Neurodevelopmental Outcome; . American Journal of Peinatology, vol. 26, No. 8 (2009).

Norihiro Sugino, "20. Management of Normal Vaginal Delivery (D. Diagnosis, Therapy and Management of Obstetric diseases", Journal of the Japanese Obstetric and Gynaecological Society, Oct. 2008, vol. 60, No. 10, pp. N-451-N-457, URL: https://dl.ndl.go.jp/view/prepareDownload?contentNo=1&itemId=info%3Andljp%2Fpid% 10720136>.

* cited by examiner

FIG. 2
Mean Postnatal Base Excess scores by Time After Birth
Categorized by Fetal Reserve Index Risk
Green-Yellow
GreenYellow
Red
Crimson
Red
Crimson
Mean
BE
(mmol/l)
-4
-6
-8
-10
-12
-14
-16
-18
4
8
16
32
64
Time after birth in minutes

METHOD AND APPARATUS FOR REDUCING THE RISK OF NEONATAL NEUROLOGICAL INJURY

CROSS-REFERENCE TO RELATED APPLICATIONS

This application is related to, and claims the benefit of priority from, U.S. Provisional Application Ser. No. 62/767,147, filed 14 Nov. 2018, and U.S. Provisional Application Ser. No. 62/791,337, filed 11 Jan. 2019. The disclosures of which are incorporated herein by reference in their entireties.

FIELD OF THE INVENTION

The invention pertains to a method and apparatus for reducing the risk of neurological injury to a neonatal human child.

BACKGROUND

It is well-known that when fetal status is compromised, any material diminution in maternal cardiac output, oxygenation of the maternal blood, or maternal uterine blood flow will place the fetus at significant subsequent risk for the development of fetal hypoxia and asphyxia (metabolic acidosis) if labor and its sequelae, often including impaired oxygenation, are allowed to continue. It is estimated that, in the United States, hundreds of fetal and early infant deaths per year are the result of intrauterine hypoxia and birth asphyxia. Several thousands have neurological compromise, including cerebral palsy and lesser forms of neurologic compromise, as categorized by measures such as the Sarnat Score. It is also widely accepted that fetal neurological injury that develops during labor results from progressive hypoxia and acidemia severe enough to produce cerebral ischemic.

Electronic fetal monitoring (EFM) was introduced into practice in the late 1960's in an attempt to permit timely intervention (e.g., expedited delivery by cesarean delivery) in situations in which the fetus appears to either be presently compromised already or will be so imminently. EFM has been widely adopted and is currently used in the vast majority of births in the United States.

The premise of EFM is the recognition of asphyxia related to metabolic acidemia. The response to fetal heart rate (FHR) patterns is predicated on the identification and "rescue" of the asphyxiated fetus, hopefully, before it has suffered damage. Traditionally, when any of the parameters of the FHM data demonstrate "reassurance," labor is allowed to continue, with intervention being reserved for the situation when these parameters are abnormal, indicative of significant asphyxia (metabolic acidosis), or an acute emergency arises (e.g., fetal bradycardia). Such interpretations are often very subjective; even experts often disagree as to the significance of individual patterns.

This approach, based on "rescue" of the fetus, has not resulted in improved outcomes either immediately or long-term. Despite obvious beneficial impacts on intrapartum stillbirth, neonatal death rates, and reduction in neonatal seizures, EFM has failed to produce the expected reduction in neonatal encephalopathy and cerebral palsy (NEACP) and long-term handicap rates. With high rates of both intra- and inter-observer error, it has been further criticized as an imprecise, subjective, and poorly predictive measure of fetal well-being with a high false-positive rate leading to unnecessary intervention, but without the discriminatory power to identify the truly hypoxic or injured fetus.

Scores of publications have both praised and criticized EFM and its contributions to modern maternity care. There are widely divergent opinions as to how much EFM has helped and hurt the practice of obstetrics. What most authorities do agree, however, is that EFM cannot clearly distinguish those fetuses already damaged prior to the onset of labor and those at serious risk of imminent danger during labor from those comfortably safe from labor. Some notable authorities have opined that even if EFM was interpreted perfectly, it would still miss about 50% of the compromised cases.

A number of published classifications and management guidelines have appeared from various sources with no apparent improvement in neurological outcome or reduction in the allegations of obstetrical negligence. For instance, the American College of Obstetricians and Gynecologists (ACOG) introduced in 2008 a three-tiered "category system" (CAT system) based on the presumed presence of fetal acidemia. Category I (CAT I) represents a completely reassuring tracing (i.e. absent acidemia). Category III (CAT III) suggests imminent danger (or presence of injury) and the need for immediate delivery from presumed acidemia to prevent or decrease worsening of the fetal injury. Category II (CAT II) shows "elements of concern", but it is "intermediate" (meaning non-diagnostic). There is no specific understanding of or agreement on how hypoxia or acidosis came to be present, or how much time the fetus has left before irreversible neurological injury occurs. There is no obvious pathophysiological basis for the ACOG's three-tiered system in FHR pattern surveillance. The CAT system can actually only serve as a diagnostic screening test for injury that has already occurred or is in the process of occurring. By the time the CAT III stage is reached, it is often already too late to effectively alter the process of fetal injury, even with emergency operative delivery.

Concomitantly, there are world-wide efforts to reduce the cesarean delivery rate in part by increasing the tolerance for increasing lengths of labor and for abnormal FHR patterns to be allowed to continue. The safety of these initiatives has been questioned. What is more, they created a conflict between individual physicians trying to limit their legal exposure from delaying cesarean deliveries, on the one hand, and the interest of hospitals and governments in keeping those numbers down.

The near ubiquitous use of EFM has also failed to lower the rate of emergency operative deliveries (EOD). EFM's performance metrics have low sensitivity, specificity, and predictive values for both cerebral palsy and EOD. There are many EODs, and the vast majority have normal outcomes. EODs, however, cause serious disruption of the delivery suite routine with increased complications, anxiety, and concern for all.

In an improvement of the conventional means for interpreting EFM data and improving fetal outcomes in labor and delivery, the inventor hereof discloses in U.S. Pat. No. 9,131,860 an apparatus for identifying the level of fetal risk during labor. The apparatus includes at least one computer operative to receive input signals indicative of at least FHR and maternal uterine activity in a patient, the at least one computer further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e). The at least one computer is further operative to (iii) receive user-inputs indicative of the presence in the patient of one or more antecedent parameters which elevate the level of fetal risk during labor, and (iv) to determine at a given point in time during labor a present level of risk to the fetus which takes into account only: the total number of the one or more antecedent clinical parameters which elevate the level of fetal risk during labor; and the total number of the parameters (a) through (e) that each simultaneously, independently exhibit at least one of the non-reassuring characteristics at the given point in time during labor. This invention has been demonstrated to yield consistent assessment of EFM data and, consequently, consistent identification of fetuses at risk for neurological injury.

In a further improvement of the conventional means for interpreting EFM data and improving fetal outcomes in labor and delivery, the inventor hereof discloses in Published U.S. Application 2019/0274618, the disclosure of which is incorporated herein by reference in its entirety, an apparatus for identifying the level of fetal risk during labor, the apparatus comprising: at least one computer operative to receive input signals indicative of at least fetal heart rate ("FHR") and maternal uterine activity in a patient, the computer operative (i) to determine baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e). The computer is further operative to (iii) receive user-inputs indicative of the presence in the patient of one or more (f) maternal risk factors, (g) obstetrical risk factors, and (h) fetal risk factors which elevate the level of fetal risk during labor, and (iv) to determine at a given point in time during labor a present level of risk to the fetus which takes into account only: the total number of the parameters (a) through (e) that are each simultaneously, independently exhibit at least one of the non-reassuring characteristics at the given point in time during labor, and the total number of the parameters (f) through (h) which are present.

While the foregoing inventions hold promise for improved outcomes in labor and delivery, neurological injury to neonates in consequence of progressive hypoxia and acidemia continues and, therefore, remains a problem in need of further solutions.

SUMMARY

There is disclosed a method and apparatus for reducing the risk of neurological injury to a neonatal human child.

In one embodiment, the method comprises the steps of:

(I) monitoring in a pregnant patient during labor at least a first set of parameters indicative of a present level of risk for neurological injury to the child as a fetus;

(II) during the period between a cervical dilatation of 10 cm in the patient and delivery of the child and/or during at least the first 5 minutes following delivery of the child, determining a present level of risk for neurological injury to the child based on the at least first set of parameters at a given point in time during labor that is between a cervical dilatation of 10 cm in the patient and delivery of the child, and wherein the determined present level of risk corresponds to one of a plurality of predetermined levels of predicted risk for neurological injury to the child as a neonate; and (III) commencing monitoring the child for one or more postnatal parameters indicative of neurological injury or its onset within the first 5 minutes following delivery of the child, and/or performing one or more measures for treating the child for neurological injury or its onset within the first 60 minutes following delivery of the child.

In one embodiment, the monitoring step (I) comprises monitoring in the pregnant patient at least each of the parameters of (a) fetal heart rate (FHR), (b) baseline FHR variability, (c) FHR accelerations, and (d) FHR decelerations to determine whether each parameter simultaneously, independently exhibits at least one non-reassuring characteristic from a plurality of pre-defined non-reassuring characteristics; and the determining step (II) comprises determining a present level of risk for neurological injury to the child which takes into account only the total number of the monitored parameters of at least (a) through (d) that each simultaneously, independently exhibit at least one of the non-reassuring characteristics at a given point in time during labor that is between a cervical dilatation of 10 cm in the patient and delivery of the child.

In another embodiment, the monitoring step (I) comprises monitoring in the pregnant patient at least each of the parameters of (a) fetal heart rate (FHR), (b) baseline FHR variability, (c) FHR accelerations, (d) FHR decelerations, and (e) maternal uterine activity, to determine whether each parameter simultaneously, independently exhibits at least one non-reassuring characteristic from a plurality of pre-defined non-reassuring characteristics; and the determining step (II) comprises determining a present level of risk for neurological injury to the child which takes into account only the total number of the monitored parameters of at least (a) through (e) that each simultaneously, independently exhibit at least one of the non-reassuring characteristics at the given point in time during labor.

According to one aspect of the invention, the step (II) further comprises assigning one of a plurality of predefined risk categories to the child based on the determined present level of risk.

In another aspect, the predefined risk categories comprise three risk categories, the determined present level of risk falls into one of the three risk categories, and the assigned category of risk corresponds to one of the plurality of predetermined levels of predicted risk for neurological injury to the child as a neonate In still another aspect, the plurality of predetermined levels of predicted risk comprise predicted Base Excess values for approximately 30 minutes post-delivery.

In certain embodiments, the method further comprises the step (IV) of identifying a potential risk for neurological injury to the child based on the one or more postnatal parameters as monitored within the first 5 minutes following delivery of the child. The one or more postnatal parameters as monitored within the first 5 minutes following delivery of the child correspond to one of the plurality of predetermined levels of predicted risk for neurological injury to the child as a neonate.

In one aspect, the one or more postnatal parameters indicative of neurological injury or its onset of step (III) are selected from among the group of neonatal blood pH, Base Excess, neonatal heart rate (NHR), and $pO_2$.

In one aspect of the present invention, the plurality of predetermined levels of predicted risk for neurological injury to the child as a neonate are derived from a dataset comprising historical determinations of risk for neurological injury based on the at least first set of parameters at a given point in time during labor that is between a cervical dilatation of 10 cm in the patient and delivery of the child, correlated with historical data of one or more postnatal parameters of neurological injury or its onset taken from the period between delivery and for at least 30 minutes thereafter.

In another aspect, the one or more measures for treating the child for neurological injury or its onset are selected from: intubating and/or oxygenating the neonatal child upon delivery and prior to clamping and cutting of the umbilical cord; intubating and/or oxygenating the neonatal child after the umbilical cord is clamped and cut; performing brain cooling; and/or performing other therapeutic measures.

The present invention further comprehends an apparatus for reducing the risk of neurological injury to a neonatal human child, comprising:

at least one computer operative to:
- receive from a monitored patient during labor input signals corresponding to at least a first set of parameters indicative of a present level of risk for neurological injury to the child as a fetus;
- receive from the neonatal child input signals corresponding to one or more postnatal parameters indicative of neurological injury or its onset;
- determine, during the period between a cervical dilatation of 10 cm in the patient and delivery of the child and/or during at least the first 5 minutes following delivery of the child, a present level of risk for neurological injury to the child based on the at least first set of parameters at a given point in time during labor that is between a cervical dilatation of 10 cm in the patient and delivery of the child, wherein the determined level of risk corresponds to one of a plurality of predetermined levels of predicted risk for neurological injury to the child as a neonate;

at least one output operatively connected to the at least one computer, wherein the at least one computer is further operative to indicate via the at least one output by no later than the first 5 minutes following delivery of the child:
- the determined level of risk and/or the corresponding one of the plurality of predetermined levels of predicted risk for neurological injury to the child as a neonate; and
- information representing the received input signals corresponding to the one or more postnatal parameters.

In one embodiment, the first set of parameters comprise (a) FHR, (b) baseline FHR variability, (c) FHR accelerations, and (d) FHR decelerations. In this embodiment, the input signals comprise at least FHR, and the at least one computer is operative to determine the parameters (a) through (d) based on the FHR input signals. The determination of the present level of risk to the child for neurological injury comprises determining whether each parameter (a) through (d) exhibits at least one non-reassuring characteristic at a given point in time during labor that is between a cervical dilatation of 10 cm in the patient and delivery of the child, and transforming the number of the parameters (a) through (d) that simultaneously exhibit at least one non-reassuring characteristic into an indication of the present level of risk to the child risk to the child for neurological injury corresponding to the number of the parameters (a) through (d) that simultaneously, independently exhibit at least one non-reassuring characteristic.

According to one aspect, the input signals further comprise input signals indicative of maternal uterine activity, the first set of parameters further comprise (e) maternal uterine activity, and the at least one computer is operative to determine the parameters (a) through (e) based on the FHR and maternal uterine activity input signals. The determination of the present level of risk to the child for neurological injury comprises determining whether each parameter (a) through (e) exhibits at least one non-reassuring characteristic at a given point in time during labor that is between a cervical dilatation of 10 cm in the patient and delivery of the child, and transforming the number of the parameters (a) through (e) that simultaneously exhibit at least one non-reassuring characteristic into an indication of the present level of risk to the child risk to the child for neurological injury corresponding to the number of the parameters (a) through (e) that simultaneously, independently exhibit at least one non-reassuring characteristic.

According to one aspect, the at least one computer is further operative to assign one of a plurality of predefined risk categories to the child based on the determined present level of risk.

According to another aspect, the predefined risk categories comprise three risk categories, the determined present level of risk falls into one of the three risk categories, and the assigned category of risk corresponds to one of the plurality of predetermined levels of predicted risk for neurological injury to the child as a neonate Per still another aspect, the plurality of predetermined levels of predicted risk comprise predicted Base Excess values for approximately 30 minutes post-delivery.

According to a still further feature, the one or more postnatal parameters indicative of neurological injury or its onset are selected from among the group of neonatal blood pH, Base Excess, neonatal heart rate (NHR), and $pO_2$.

As with the method of the invention, the plurality of predetermined levels of predicted risk for neurological injury to the child as a neonate are derived from a dataset comprising historical determinations of risk for neurological injury based on the at least first set of parameters at a given point in time during labor that is between a cervical dilatation of 10 cm in the patient and delivery of the child, correlated with historical data of one or more postnatal parameters indicative of neurological injury or its onset taken from the period between delivery and for at least approximately the first 30 minutes thereafter. The first set of parameters comprise, in one embodiment, (a) FHR, (b) baseline FHR variability, (c) FHR accelerations, and (d) FHR decelerations, and the one or more postnatal parameters comprise Base Excess. In another embodiment, the first set of parameters further include (e) maternal uterine contractions.

BRIEF DESCRIPTION OF THE DRAWINGS

The present invention will be appreciated from the following description and accompanying drawings, of which:

FIG. 1 charts the median Base Excess values; FIG. 2 charts the mean Base Excess values; and FIG. 3 charts the multiple of median (MoM) for the Base Excess values.

FIG. 4 charts the median pH values; FIG. 5 charts the mean pH values; and FIG. 6 charts the multiple of median (MoM) for the pH values.

FIG. 7 charts the median heart rates; FIG. 8 charts the mean heart rates; and FIG. 9 charts the multiple of median (MoM) for the heart rates.

FIG. 10 charts the median $pO_2$ values; FIG. 11 charts the mean $pO_2$ values; and FIG. 3 charts the multiple of median (MoM) for the $pO_2$ values.

FIG. 13 charts the median reactivity values; and FIG. 14 charts the mean reactivity values.

WRITTEN DESCRIPTION

Figure 1:
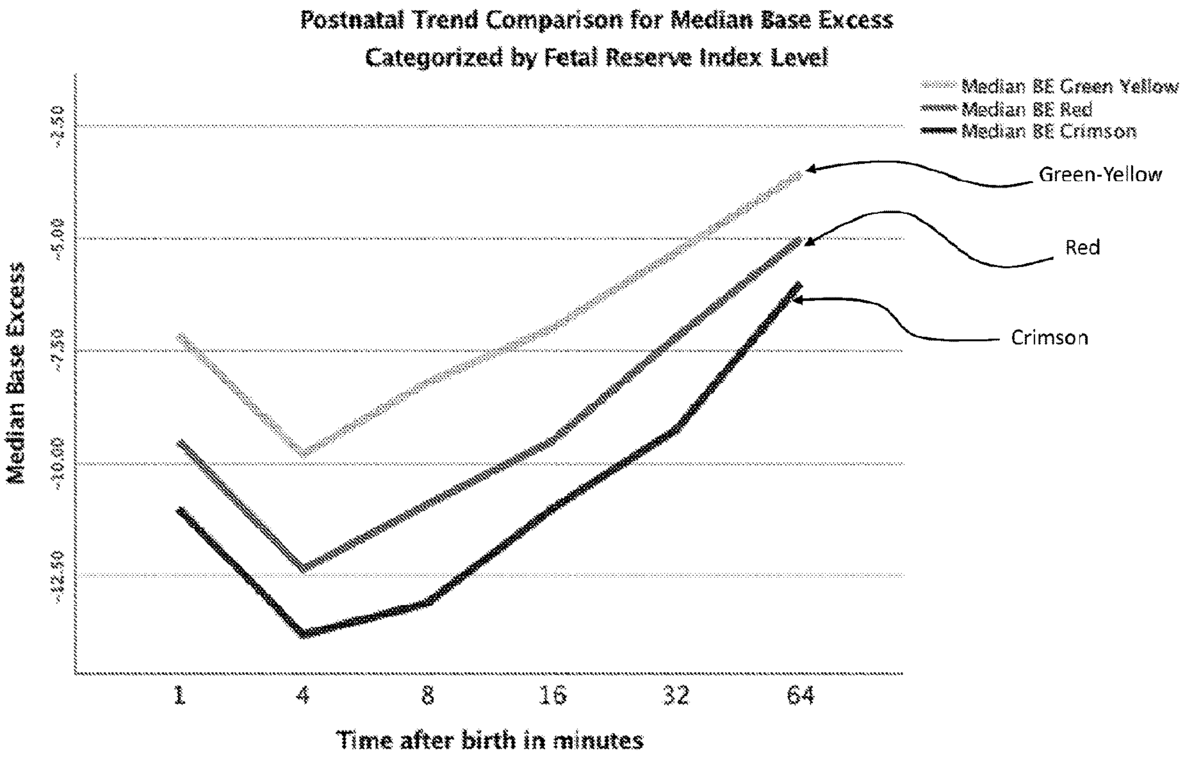
FIGS. 1 through 3 are graphs comparing the change over time for the monitored neonatal parameter of Base Excess for study populations of neonates grouped according to their FRI scores.

As required, detailed embodiments of the present invention are disclosed herein. However, it is to be understood that the disclosed embodiments are merely exemplary of the invention that may be embodied in various and alternative forms. The accompanying drawings are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention comprehends a method and apparatus for reducing the risk of neurological injury to a neonatal human child within a period of time promptly following delivery.

As used herein, "child" is intended to comprehend the human child both prior to delivery (i.e., the child as a fetus) and subsequent to delivery (i.e., the neonatal child). The terms "fetus" and "child as a fetus" are used interchangeably, as are the terms "neonate" and "neonatal child." In context, "child" also refers to the child as a fetus and as a neonate.

As set forth in the disclosure of Published U.S. Application 2019/0274618, converging patterns signal the onset of neurologic injury to the fetus. While these patterns are seen in labor, however, they are rarely seen during operative delivery, at least in part because fetal monitors (e.g., the fetal scalp monitor, or FSE) are removed during the procedure. Instead, assessment of newborn health has primarily been through the Apgar score and, in more complex cases, periodic measurements of pH, bicarb, and Base Excess which. Continued and recorded heart rate monitoring, as is done prenatally, is not part of the routine.

It has also been generally presumed that adaptation from fetal to neonatal life generally proceeds smoothly from birth. One commonly accepted notion in these regards is that Base Excess improves by 0.1 units per minute from cord blood assessment. Nonetheless, the inventor hereof has discovered that conversion can and does occur during the initial minutes of neonatal resuscitation when the neonate has trouble converting from fetal to adult circulation. A basic understanding of the processes associated with fetal and adult circulation is illustrative.

The ductus arteriosus is open during fetal life so that blood exits the right ventricle. It comes mostly from the superior vena cava that enters the right atrium and traverses the tricuspid valve into the right ventricle, which then traverses the pulmonic valve. This deoxygenated blood enters the aorta from the open ductus and, without brain sparing, goes towards the placenta and body of the fetus. With brain (or head) sparing as seen in intrauterine growth restriction (IUGR), the peripheral resistance increases and more of the deoxygenated blood is redirected to the brain (increased UA S/D ratio, lowering of MCA ratio). Increased risks of intracerebral hemorrhage and infarction are due to increasing blood flow, albeit with less oxygenated blood.

During normal neonatal resuscitation, the lungs expand. Surfactant opens the alveoli and bronchioles; the foramen ovale and the ductus arteriosus close. Oxygen that enters the lungs is then picked up by the blood from the right ventricle and returns, via the pulmonary artery, to the left atrium, exiting through the mitral valve into the left ventricle and out the aortic valve to the aorta and the brain and body.

Persistent fetal circulation occurs in the acidotic or compromised fetus. After the cord is clamped, the lungs may expand with ventilation, but the blood flow remains decreased due to persistent traversing of the foramen ovale and ductus arteriosus which results in non-oxygenated blood being sent to the brain. With increased systemic vascular resistance, the brain can experience hypoxia, infarcts, and intracerebral hemorrhage. As the ductus and foramen close, the oxygenation improves. However, in the compromised fetus, the inventor hereof hypothesizes that it may be significantly limited, and the conversion delayed, or even that it may not occur at all. Instead, spasms or trickles occur. Blood flow to the brain increases as the fetus improves with resuscitation.

After delivery, once the umbilical cord is clamped, there exists a critical period in which to establish postnatal brain oxygenation. In adults, only 3 minutes of anoxia is required for brain damage. On the other hand, the in-utero, non-cord-clamped fetus has perhaps 15 minutes prior to the irrevocable occurrence of brain damage. The inventor hereof theorizes that it is during these first few minutes (approximately 5 minutes) of neonatal life when the compromised fetus, with a decreased fetal reserve and borderline oxygenation, is often neurologically injured. That is, the cause of damage to the neonate comes from delayed conversion from fetal to neonatal circulation. Unfortunately, such injury is not recognized by current neonatal assessments. Therefore, no matter how good the immediate neonatal resuscitation appears to be, the already compromised neonate may suffer neurological injury under conventional delivery protocols.

Having recognized this mechanism for neurological injury and a means of identifying the potential risk far earlier than has heretofore been possible, the inventor proposes a method and apparatus for reducing the risk of neurological injury to the neonate.

Generally, the method comprises the steps of: (I) monitoring in a pregnant patient during labor at least a first set of parameters indicative of a present level of risk for neurological injury to the child as a fetus; (II) during the period between a cervical dilatation of 10 cm in the patient and delivery of the child and/or during at least the first 5 minutes following delivery of the child, determining a present level of risk for neurological injury to the child based on the at least first set of parameters at a given point in time during labor that is between a cervical dilatation of 10 cm in the patient and delivery of the child, and wherein the determined present level of risk corresponds to one of a plurality of predetermined levels of predicted risk for neurological injury to the child as a neonate; and (III) commencing monitoring the child for one or more postnatal parameters indicative of neurological injury or its onset within the first 5 minutes following delivery of the child, and/or performing one or more measures for treating the child for neurological injury or its onset within the first 60 minutes following delivery of the child.

Fetal Monitoring

In the exemplary embodiments of the invention described herein, the patient is monitored during labor for at least a first set of parameters that are employed to establish a level of risk for neurological injury to the child. These parameters comprise a plurality of variable, dynamic parameters associated with EFM, including (a) baseline FHR, (b) baseline FHR variability, (c) FHR accelerations, and (d) FHR deceleration. Optionally, these parameters also include a dynamic parameter (e) maternal uterine activity (i.e., uterine contractions) associated with intrauterine activity ("IUA"). In this context, the monitored patient refers to the mother and/or the fetus, as appropriate to the monitored parameters. In the exemplary embodiment, these parameters, as monitored, are assessed for assurance or non-reassurance according to the characteristics set forth in Table 1 below.

TABLE 1

EFM and IUA Variables

| | Reassuring | Non-Reassuring (Point A) |
|---|---|---|
| Uterine contractions | ≤8/20 Minutes | >8/20 Mins |
| FHR baseline variability | 5-25 BPM | <5 or ≥15 BPM |
| FHR accelerations | >15 × 15 BPM/15 Secs | <15 BPM/15 Secs |
| FHR decelerations | No late return to baseline | Late return to baseline (i.e. +OCT) |
| Baseline FHR (BPM) | 110-160 BPM | >15 BPM Rise since admission (<160) |

Optionally, the monitored parameters may also include certain additional maternal, obstetrical, and fetal risks ("MOFR") factors (separate from EFM variables), as follows: (f) Maternal risk factors, (g) Obstetrical risk factors, and (h) Fetal risk factors (separate from EFM). Per this example, the parameter (f) of "Maternal Risk Factors" comprehends the following non-reassuring characteristics:

1) Decreased cardiac output/vascular perfusion of the placenta
   a. Cardiac Disease with risk of decreased cardiac output in pregnancy
   b. Hypertension (Chronic and Pregnancy induced)
   c. SLE (systemic lupus erythematosus), etc.
2) Oxygen carrying capacity
   a. Pulmonary disorders (e.g. Asthma)
   b. Anemia and Hemoglobinopathy
3) Infection (chronic and acute)
4) Chronic debilitating disease
5) Malabsorption/Poor weight gain
6) Endocrine—Diabetes and Thyroid disorders
7) Advanced maternal age
8) Drug abuse, addiction, and smoking
9) Obesity—BMI (body mass index) >35
10) Short stature (≤5'2")
11) Epidural anesthesia Per this example, the parameter (g) of "Obstetrical Risk Factors" comprehends the following non-reassuring characteristics:

1) IUGR (intrauterine growth restrictions)/Macrosomia
2) Oligohydramnios
3) Polyhydramnios
4) Bleeding and abruption
5) Previous cesarean section
6) Placental and umbilical cord anomalies
7) Rupture of membranes (PPROM—preterm or premature rupture of membranes, SROM—spontaneous rupture of membranes, AROM—artificial rupture of membranes)
8) Dystocia (protraction and arrest disorders of labor)
9) Malpresentation Finally, per this example, the parameter (h) of "Fetal Risk Factors" comprehends the following non-reassuring characteristics:

1) Abnormal Dopplers/BPP (biophysical profile)
2) Genetic disorders
3) Fetal arrhythmia
4) Meconium passage
5) Chorioamnionitis
6) Second stage of labor—pushing
7) Amnioinfusion
8) Discontinuation of Pitocin due to fetal intolerance
9) Conversion patterns (acute prolonged tachycardia (>170 bpm))
10) Ominous overshoots
11) Bradycardia (<100 bpm)
12) Missing important data in labor (e.g. lack of EFM in second stage)

Interpretation of the various parameters described above may be done per convention, including, optionally, using the methodology disclosed by the inventor hereof in U.S. Pat. No. 9,131,860 and Published U.S. Application 2019/0274618. More particularly according to one embodiment disclosed in those references, the method most generally comprises determining whether each monitored or evaluated parameter independently exhibits at least one non-reassuring characteristic, such as, for instance, the non-reassuring characteristics discussed above; and deriving an indication, referred to as the "Fetal Reserve Index" (FRI) score, of the present level of risk corresponding to the number of these parameters which simultaneously, independently exhibit at least one non-reassuring characteristic/are present. Per that exemplary methodology, the number of parameters that simultaneously, independently exhibit at least one non-reassuring characteristic, on the one hand, and the indication of the present level of risk for neurological injury, on the other hand, is directly related. Thus, for instance, the highest level of risk for neurological injury according to the method wherein the parameters (a) through (e) are monitored corresponds to the simultaneous, independent exhibition of at least one non-reassuring characteristic for/presence in the patient of each of the parameters (a) through (e), while the lowest level of risk to of neurological injury corresponds to the absence of any exhibited non-reassuring characteristics for/presence in the patient of any of these parameters.

It will be appreciated that the parameters (a) through (e) are dynamic parameters; that is, they are subject to change in either direction (e.g., from normal, or reassuring, to abnormal, or non-reassuring, and back again) during the course of monitoring. On the other hand, the MOFR parameters (f) through (h) are unidirectional in nature; that is, once (and if) they occur (whether during the course of labor or even before), they negatively affect the FRI score. It will also be appreciated that the occurrence of a non-reassuring characteristic for each parameter (f) through (h) is, per the exemplary embodiment, sufficient to negatively affect the FRI score. It is unnecessary, for instance, that the parameter (f) of "Maternal Risk Factors" display more than one of the eleven exemplary non-reassuring characteristics listed above.

"Simultaneous" in the context of this disclosure means at the exact same or, at least, at the point in time during labor when the determination of assurance/non-reassurance for each monitored parameter overlaps. In an exemplary embodiment, this assessment of risk is made in 20-minute intervals coinciding with the determination of assurance/non-reassurance for the IUA parameter (e).

"Independent" in the context of this disclosure means that the exhibition/non-exhibition of one or more non-reassuring characteristics by each monitored parameter affects the determination of the present level of risk without regard to the exhibition/non-exhibition of one or more non-reassuring characteristics by any other monitored parameters. That is, while the exhibition/non-exhibition of each monitored parameter will collectively affect the determined present level of risk, each monitored parameter is considered independently of the others in respect of displaying reassuring/non-reassuring characteristics.

In an exemplary embodiment, the FRI score is derived as follows: Each of the monitored parameters (e.g. (a) through (h)) is assigned a first numerical value (e.g., "1") if the parameter was deemed normal (i.e., reassuring) and a second numerical value (e.g., "0") if abnormal (i.e., non-reassuring). The first and second numerical values are the same for each parameter. That is, only two values are employed (e.g., a 1 or a 0). The FRI score per this example is calculated on the number of points divided by the number of parameters involved (e.g., 5) and multiplied by 100 to give a percentage. As an example, a total of 5 monitored parameters ((a) through (e)) would yield a FRI score calculated as the number of points divided by 5 and multiplied by 100 to give a percentage. A total of 5 parameters ((a) through (e)) being normal would result in a FRI score of 100% (5/5), whereas a loss in points—as a function of the presence of abnormal or non-reassuring characteristics for any of the monitored FRI parameters (a) through (e)—would result in an FRI score of 80% (4/5), 60% (3/5), 40% (2/5), 20% (1/5), and 0% (0/5). Alternatively, a total of 8 parameters ((a) through (h)) being normal would result in a FRI score of 100 (8/8), whereas a loss in points—as a function of the presence of abnormal or non-reassuring characteristics for any of the monitored FRI parameters (a) through (h)—would result in an FRI score of 100% (8/8), 87.5% (7/8), 75.0% (6/8), 62.5% (5/8), 50.0% (4/8), 37.5% (3/8). 25.0% (2/8), 12.5% (1/8) and 0% (0/8).

Per exemplary embodiments, identification of the present level of risk for neurological injury is at least made by considering each parameter (e.g., (a) through (h)), when present, independently from the other parameters. Thus, the schemes for identifying a present level of risk that are within the scope of this invention are not, as is the case with some conventional methodologies, the consequence of interdependence between any parameters but, rather, are strictly a function of the number of parameters which are present in a patient and/or simultaneously, but independently, non-reassuring in their exhibited characteristics. Consistent with the foregoing, this methodology is also distinguished in that it does not take into account the degree of non-reassurance indicated by the one or more characteristics of any monitored parameters. Rather, the parameters are preferably weighted equally so that any exhibition of non-reassurance according to the predetermined non-reassuring characteristic(s) for the parameters (e.g., (a) through (e) or (a) through (h)) will cause each such parameter to contribute equally to the presently identified level of risk.

It is also contemplated by the exemplary embodiments that the method of the present invention comprehends assigning a predefined risk category to the child, wherein the predefined risk category corresponds to the determined present level of risk. For instance, the present level of risk for neurological injury may be identified both by a specific FRI score, as discussed above, and/or a grade for easy interpretation. For example, and without limitation, the "grade" of an example takes the form of arbitrary color zones, akin to traffic lights. In the example of this disclosure, the lowest level of present risk is identified as the "green zone" and comprehends FRI scores >50%. An increased (relative to the lowest level) level of present risk to the fetus is identified as the "yellow zone" and comprehends FRI scores ≤50%, and >26%. The highest level of present risk is identified as the "red zone" and comprehends FRI scores ≤25%.

With respect to therapeutic measures or other intervention, an FRI score in the "green zone" would signal no cause for action according to the exemplary scheme. Comparatively, an FRI score in the "red zone" is not to be taken as a call for immediate delivery, but rather as a cause for immediate attention by senior staff, who can evaluate the situation. During labor, intrauterine resuscitation efforts should usually be the first course of action, such as: stopping oxytocin, repositioning the patient, increasing IV fluids, and administration of oxygen by mask. Entering the "red zone" should also start a countdown to intervention, and an exemplary management protocol is to allow up to 40 minutes to get out of the red zone. Failure to do so would start a 30 minute to delivery protocol, as per the ACOG guidelines. In the "yellow zone," similarly, it is recommended under the exemplary scheme that the clinician's attention to the potential need for intervention should be heightened.

Neonatal Monitoring

In the embodiments of the invention described herein, the neonate is monitored for one or more postnatal parameters indicative of neurological injury or its onset. These parameters include, by way of non-limiting example, the following: (i) neonatal heart rate (NHR), including variability, time to recovery of variability, and time to return to baseline; (ii)

the Base Excess value (as determined from blood gas analysis, for instance); and (iii) $pO_2$.

Per this exemplary embodiment, NHR comprehends the "baseline rate" (i.e., the average heart rate measured over 10 minutes but excluding contractions), where the non-reassuring characteristic for the baseline rate is any of a heart rate of more than 165 bpm or a heart rate of less than 100 bpm, the duration of such elevated or decreased heart rate, as well as the duration of decreased heart rate variability.

Per this embodiment, "Base Excess" refers to the amount of base or acid that would have to be added to one liter of the neonate's blood to restore it to a physiological level of 7.4 at a pCO2 of 40 mmHg at 98.6° F. (37° C.). A lower than average Base Excess is non-reassuring, and a value of ≤−12 mIU/ml is considered to be at high risk for neurological damage.

Also, per this embodiment, "$pO_2$" refers to umbilical cord oxygen (16.3 mmHg is a median value). A lower than average $pO_2$ is considered non-reassuring.

These parameters (i) through (iii) may be monitored and evaluated per conventional means.

Of course, it will be appreciated that the foregoing parameters are neither exclusive nor exhaustive. Other parameters include, by way of non-limiting example, respiration rate, movement, tone, and color (APGAR score).

The period of time for monitoring is, according to the present invention, at least from the time of delivery of the neonate and thereafter for, by way of non-limiting example, anywhere from 1 to 2 hours or as soon as it is determined from these postnatal indicators that the neonate is no longer at risk of neurological damage.

Experimental Data

The evaluation of historic fetal and neonatal data corresponding to various parameters (e.g., FHR, NHR, pH, Base Excess, etc.) validates the inventor's hypothesis, as well as the utility of the present invention in reducing the risk of neurological injury to the neonate.

More particularly, data from 251 records of high-risk, term singleton pregnancies were used to assess the relationship between FRI and the EFM tracing, the course of labor, and the neonatal outcome in the first hour of life. These data were collected in the 1970s, mostly at the University of Southern California—LA County Hospital and some at Yale New Haven Hospital. Each case was supervised by an attending MFM faculty physician. The monitoring strips had 5 data lines (EFM, contraction pattern, expanded variability tracing, maternal respirations, and maternal heart rate). After delivery, the analysis continued with continuous neonatal heart rate (NHR), respirations, ECG, and indwelling catheter for blood pressure, pH, and umbilical artery core blood (CB) BE and $pO_2$. Contemporaneous annotations were provided along the entire record for scalp sampling, its results (e.g. pH, Base Excess, $pO_2$), blood pressures, drugs administered, anesthesia provided, and other relevant data. Prenatally, scalp sampling was done as indicated and recorded on the monitor strips. Postnatally, cord gases were routinely obtained at 1, 4, 8, 16, 32, and 64 minutes. Neonatal observations included: 1- and 5-min Apgar scores, NHR with time to return to predelivery rate and reactivity, and umbilical artery pH, BE, and $pO_2$. The majority of these records had all of the foregoing measurements.

The cesarean delivery rate for the 251 patients was 4.5%, with assisted deliveries at 20%.

All monitoring began, in the presence of rupture of membranes, with fetal scalp electrodes (FSE) and intrauterine pressure catheter (IUPC) in place. NHR was recorded continuously—similar to intrapartum FHR.

These data were primarily evaluated for relationships of the last FRI score to immediate NHR pattern and umbilical/neonatal acid-base balance.

According to ACOG criteria for hypoxic ischemic encephalopathy (HIE), there were no severely compromised babies in the dataset, so the worst 25% of cases at 32-min readings were used as a dependent variable in the evaluation of these data.

A Kaplan-Meier analysis was performed for BE for time to recover to a safe level of ≥−12 mmol/L BE. Converging binary logistic and ordinary least squares (OLS) regressions evaluated changes occurring immediately postpartum for BE. Sensitivity improvements were also evaluated by combining a second test (e.g. FRI+CB & UA BE).

Since pH and Base Excess are so highly correlated (r=0.63, sig <0.001), only Base Excess was used in the regression analyses to reduce collinearity problems.

NHR features (variability, accelerations, and decelerations) were interpreted with current ACOG Categories i-iii (CAT), though without contractions at predetermined intervals (1, 5, 10, 20, 30, 40, 50, 60 min). For the neonate, assessment was made of maximal NHR, Apgar scores, time to resumption of normal baseline rate, and variability after delivery. A neonatal pattern that appeared to be markedly abnormal was defined as "neonatal Category III" (NCATIII) to include all of the following that persisted for the first 10 min of life: (1) severe neonatal tachycardia (≥180 bpm) with or without a slow return (late recovery) following delivery (terminal deceleration or bradycardia at delivery), (2) absence of reactivity, and (3) decreased or absent variability.

No fetus had an umbilical artery cord blood pH ≤7.00 or 5-min Apgar score ≤3. Seven babies had umbilical cord arterial blood pH between 7.03 and ≤7.10, and all had 5-min Apgar scores ≥7. All six babies with 5-min Apgar scores between 4 and 6 had umbilical cord arterial blood pH >7.20. No fetus demonstrated a CAT III tracing. 37 fetuses (14.8%) were CAT I; and 214 fetuses (85.2%) were categorized as CAT II.

Continuous EFM and clinical data from the above-described dataset were assessed retrospectively per the FRI score determination described above, with a primary objective of evaluating the relationship of the last FRI score before delivery to immediate NHR pattern and umbilical/neonatal acid-base balance.

The results of FRI scoring were divided into three groups for purposes of further analysis. Those patients whose last (and usually worst) FRI score prior to delivery was either in the green or yellow zone (i.e., FRI score=37.5%-100%) were labeled as "green-yellow." To achieve a more linear distribution, those patients whose last FRI score was in the red zone were divided into two sub-groups: "Red," which represents FRI scores of >12.5% to ≤25%; and "crimson" (FRI score is 0%).

Patient demographics by FRI category were not different.

Figure 4:
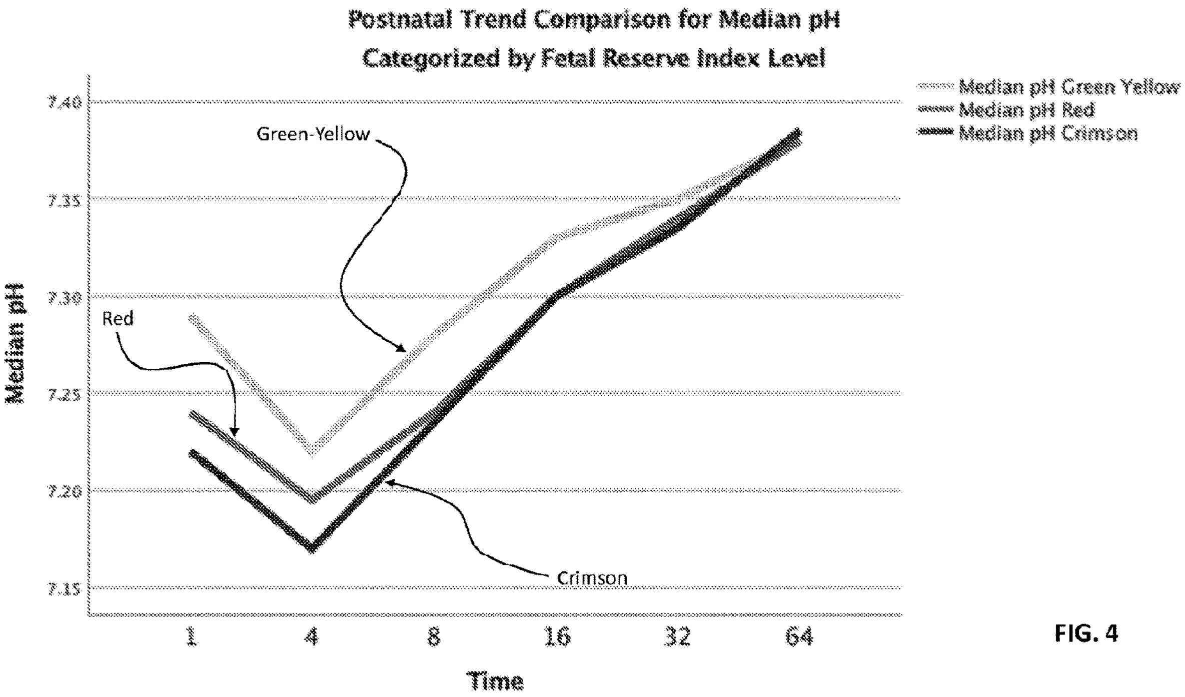
FIGS. 4 through 6 are graphs comparing the change over time for the monitored neonatal parameter of pH for neonates grouped according to their FRI scores.
Figure 5:
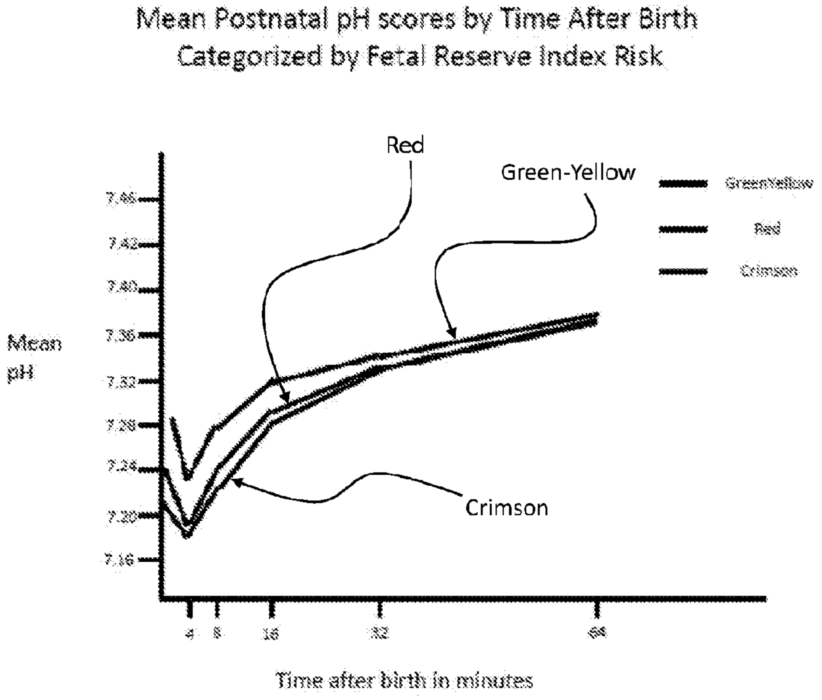
Figure 6:
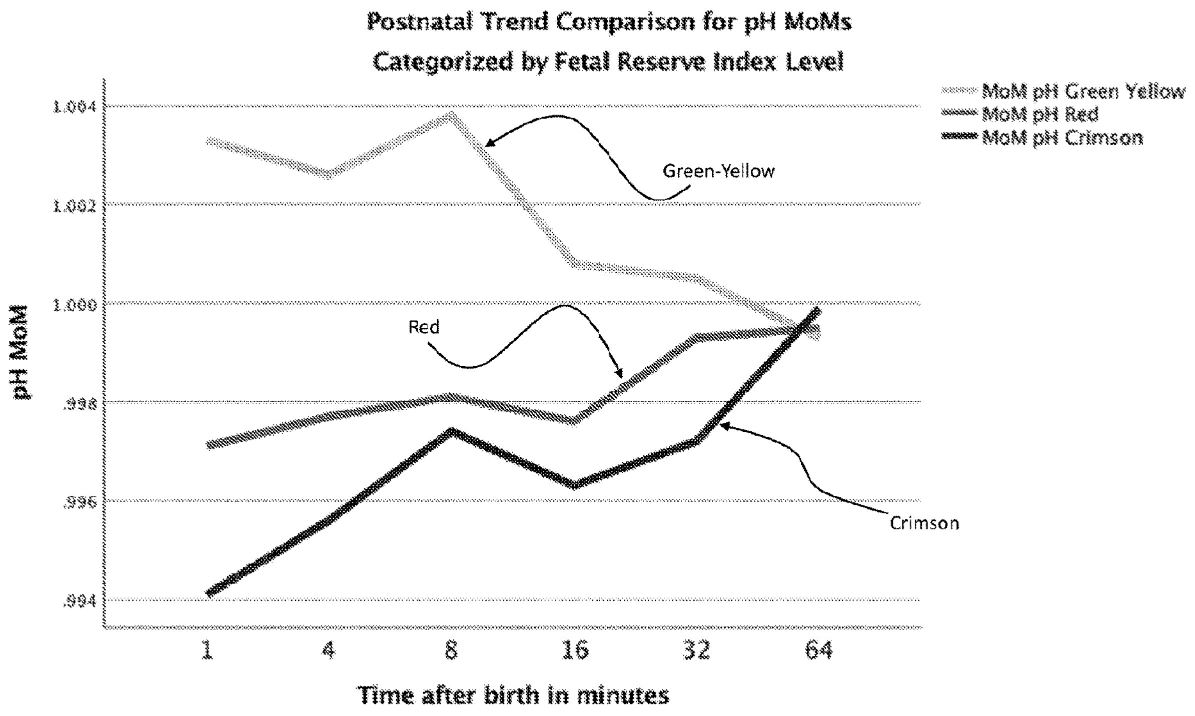
Figure 8:
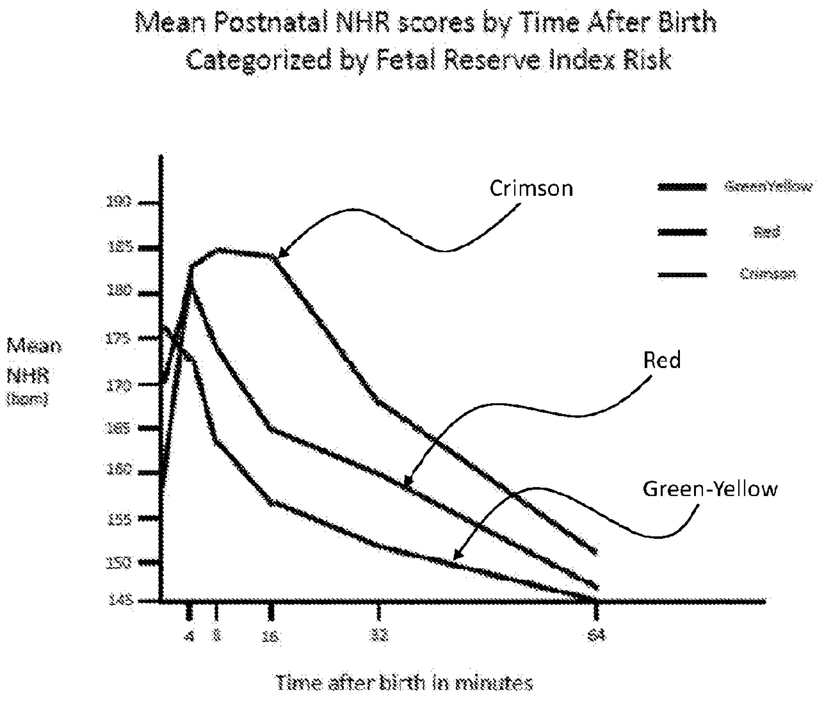
Figure 9:
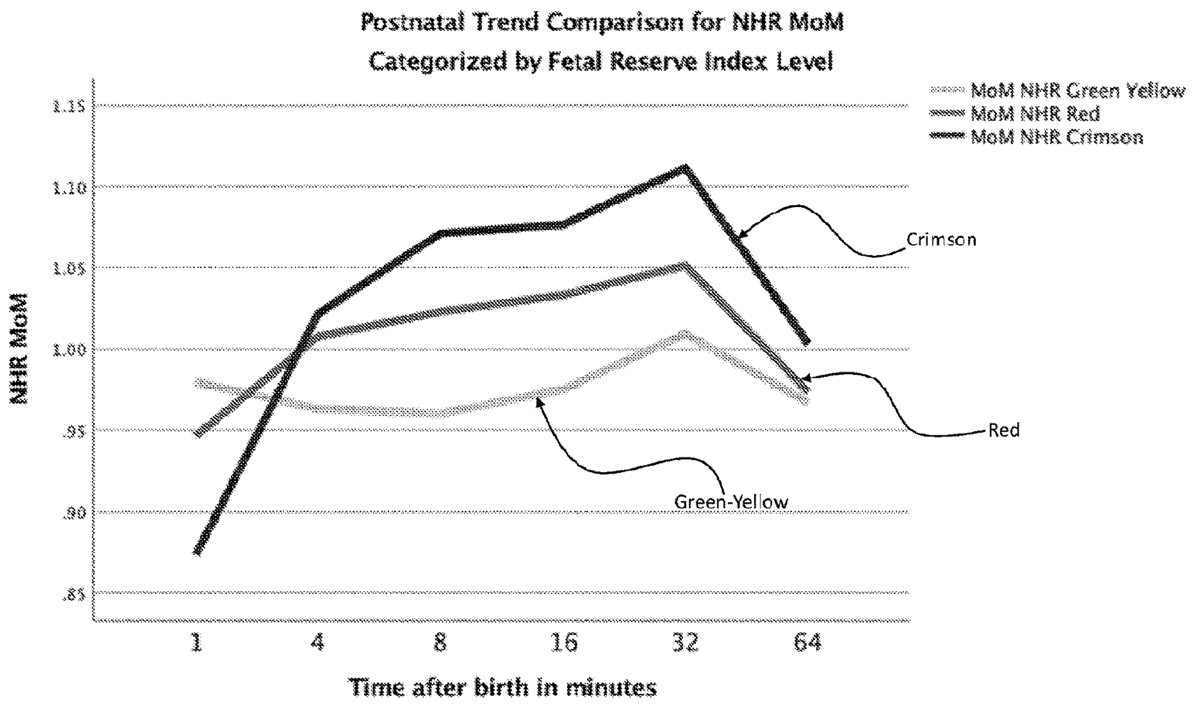
Figure 10:
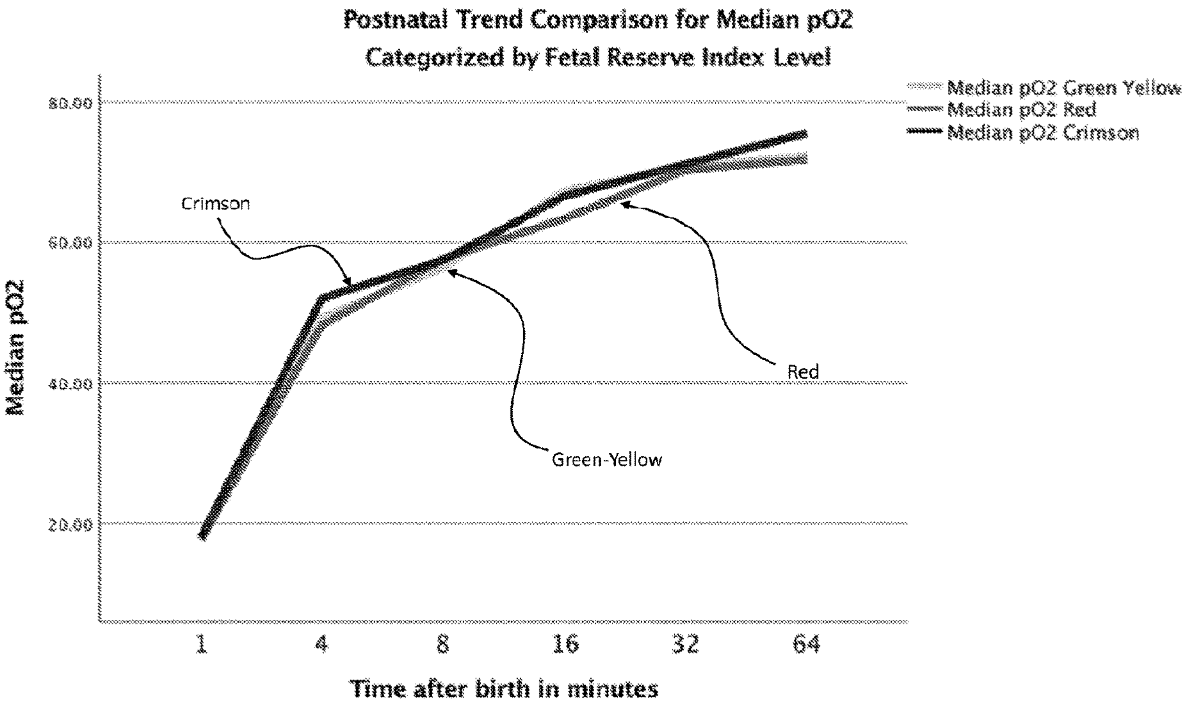
FIGS. 10 through 12 are graphs comparing the change over time for the monitored neonatal parameter of $pO_2$ for neonates grouped according to their FRI scores.
Figure 11:
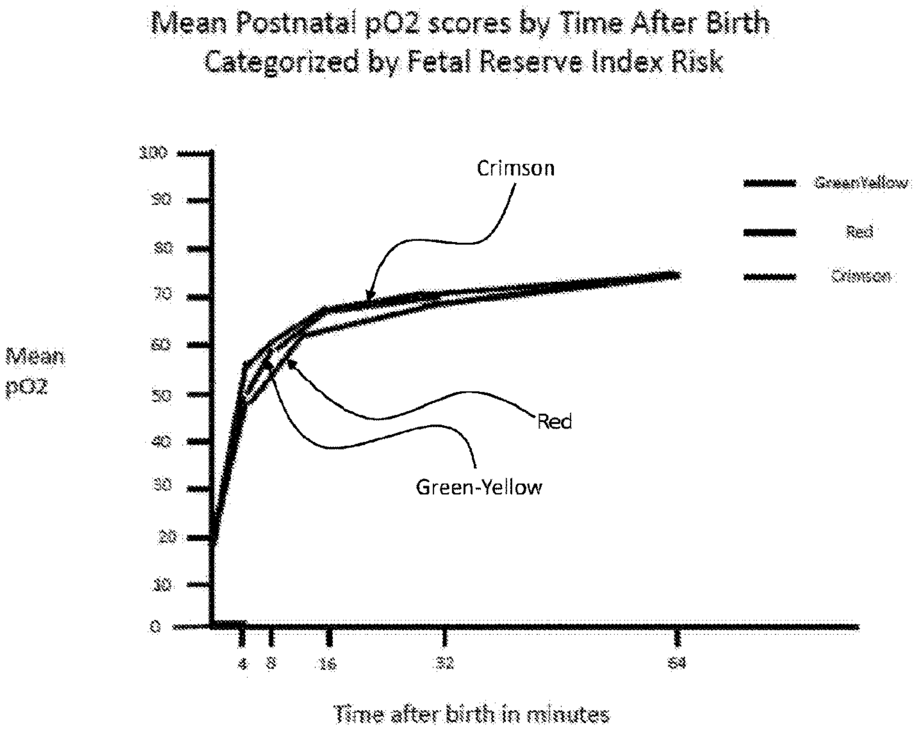
Figure 12:
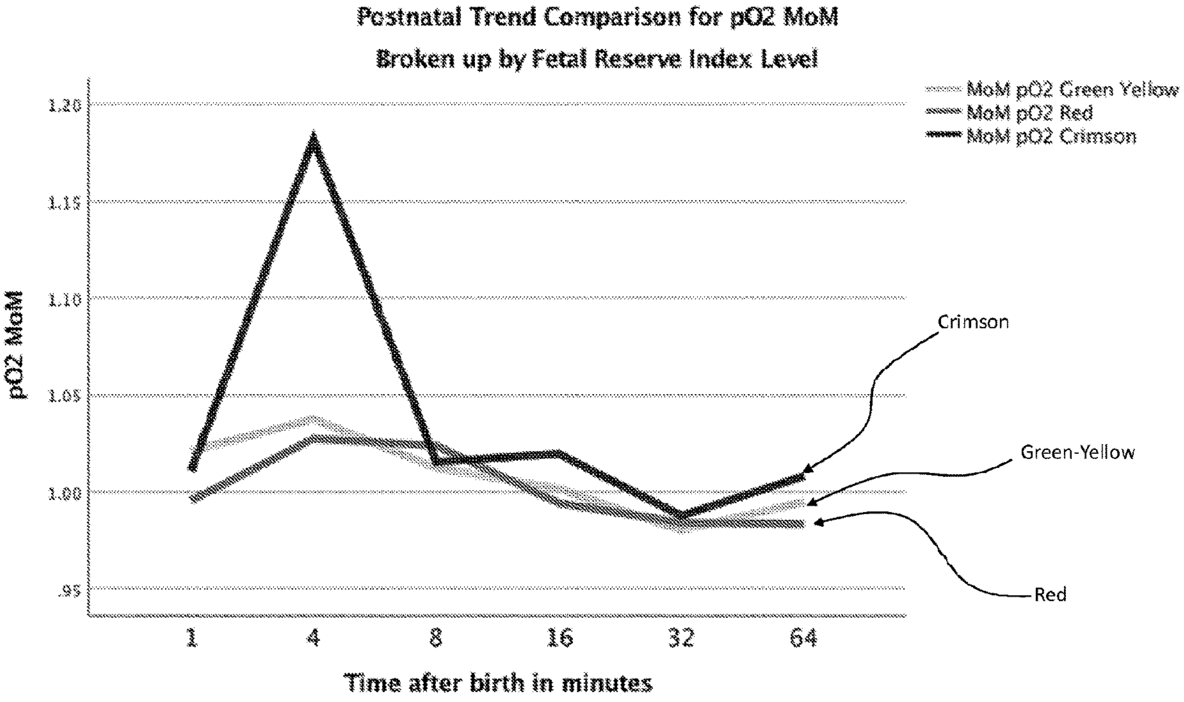
Figure 13:
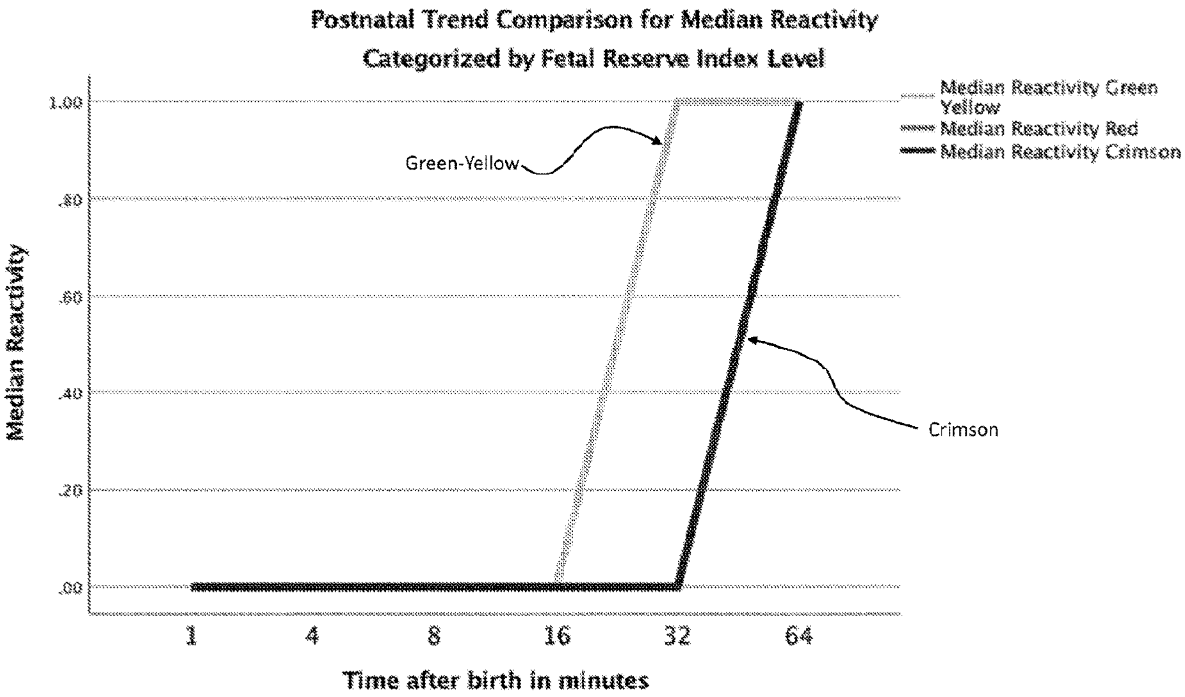
FIGS. 13 and 14 are graphs comparing the change over time for the monitored neonatal parameter of reactivity for neonates grouped according to their FRI scores.
Figure 14:
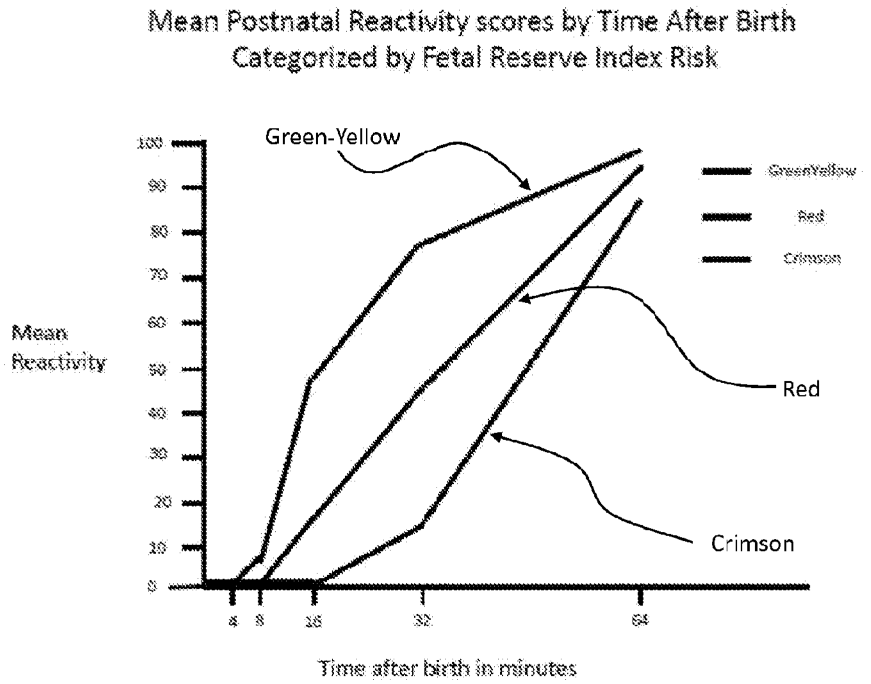
Figure 15:
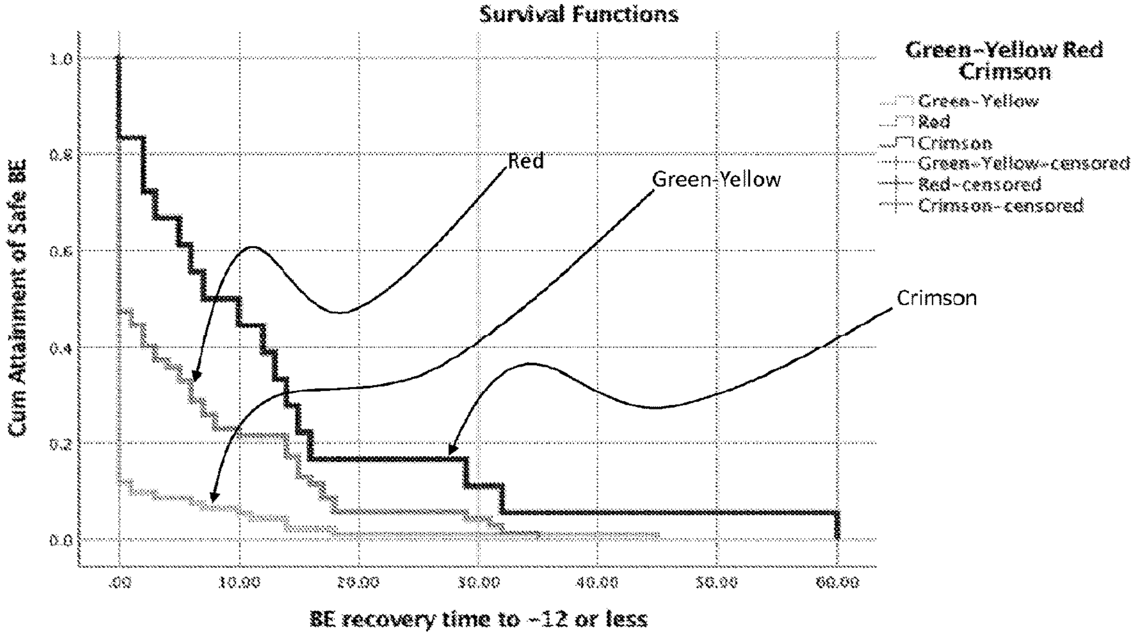
FIG. 15 is a is a Kaplan Meier graph showing the correlation between the level of the FRI scores with the period of time the neonate is exposed to "high risk" (defined, in the exemplary embodiment, as a Base Excess worse than −12).

FIGS. 1 through 14 comprise graphs comparing the change over time for various monitored neonatal parameters from the historical data, including Base Excess (FIGS. 1-3), pH (FIGS. 4-6), heart rate (FIGS. 7-9), $pO_2$ (FIGS. 10-12), and reactivity (FIGS. 13-14). FIG. 15 shows the correlation between the level of the FRI scores with the period of time the neonate is exposed to "high risk" (defined, in the exemplary embodiment, as a Base Excess worse than −12).

These graphs show the trends in these monitored neonatal parameters over time following birth (in minutes, measured from approximately 1 minute post-birth to approximately 64 minutes post-birth), wherein the post-birth data are further grouped according to the FRI score determined for these historical data from evaluation of the FHR tracings.

Figure 2:
Figure 3:
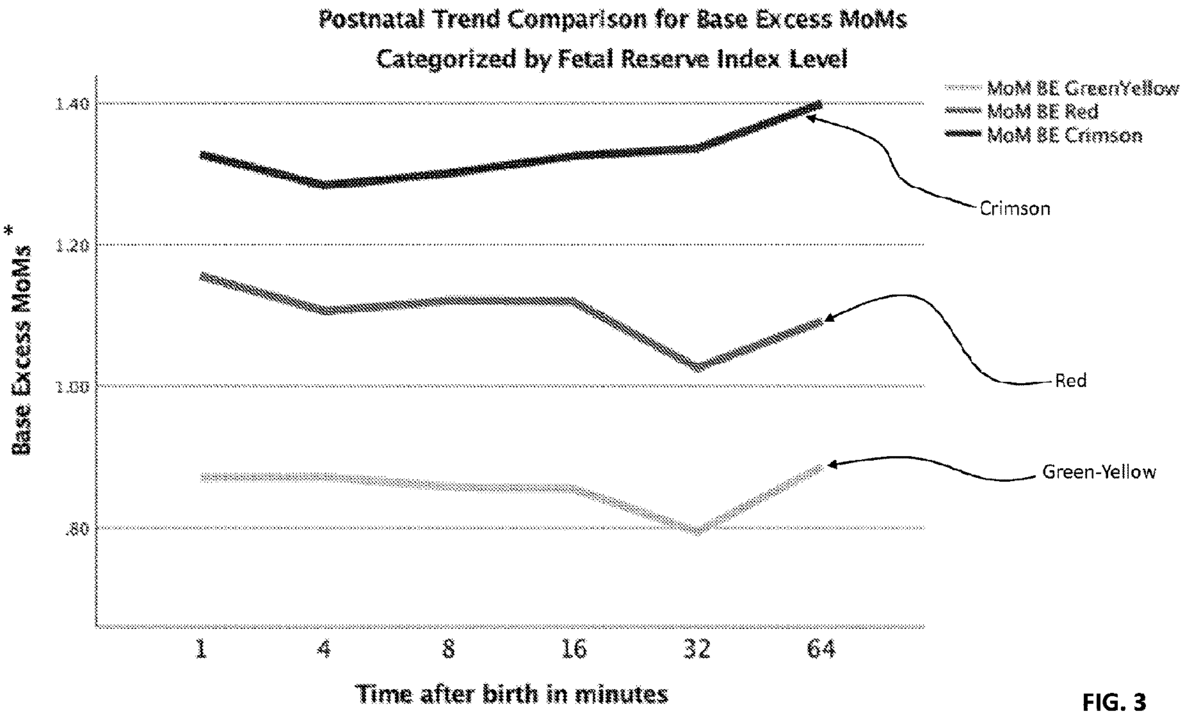

With particular reference to FIGS. 1-3, it should be noted that both the median (FIG. 1) and individual scores for Base Excess are almost always negative. When the individual Base Excess score is divided by the median Base Excess score, therefore, the result is a positive number, as reflected in FIG. 3. In the case of Base Excess, the "Crimson" FRI group is always larger than the median, (i.e., more than 1) and the Green/Yellow group is always lower than the median (i.e., less than 1). This is shown in the chart of FIG. 3.

As the graphs of FIGS. 1 through 15 generally reflect, lower FRI scores translate into non-reassuring values for the monitored neonatal parameters of Base Excess, pH, heart rate (NHR), $pO_2$ and reactivity during at least part of the period from approximately 1 minute post-birth to approximately 64 minutes post-birth. Stated another way, the worse-off the neonate is at birth in terms of the FRI score, the more the metabolic state continues to worsen over the next several minutes, and the longer it takes before the monitored parameters recover and reach reassuring values. The slopes and patterns of recovery of both pH and Base Excess were very similar, showing what appear to be 3 parallel curves for the parameters; the major differences were the values obtained from cord blood, how far the values fell, either at 4 or 8 minutes before recovery began, and how long the Base Excess remained at ≤−12 MIU/ml (which is generally considered in the literature to be the point at which there is real risk for neurological damage).

With respect to FIG. 15 in particular, the time for each group (Crimson, Red, and Green-Yellow) to recover to a safe BE (−12 or better) is shown. For the Crimson FRI group, about 42% of neonates are still at or worse than −12 BE at 10 minutes post-delivery. For the red FRI group, 21% are still at −12 BE or worse at 10 minutes post-delivery. Finally, for the green-yellow FRI group, only about 8% of neonates failed to yet attain a safe BE level at 10 minutes post-delivery. These are dramatic and persistent differences, as attested to by the shape of these curves. In comparison, about 18% of the crimson FRI group are still not in the safe BE zone at 20 minutes post-delivery, while about 8% of the red FRI group are not yet in the safe BE zone, and only a very few of the green-yellow FRI group have yet to attain a safe BE score (better than −12, per the example).

A pH of <7.00 and Base Excess of <−12 have often been considered thresholds for risk for CP and neurologic compromise.

These results further suggest that the neurological compromise seen in some babies who do not meet the standard criteria of pH <7.00 and Base Excess <−12 prenatally may actually be occurring in the early postnatal period rather than in utero. This is because it is only during this period that the values deteriorate beyond the commonly accepted threshold for concern.

Figure 7:
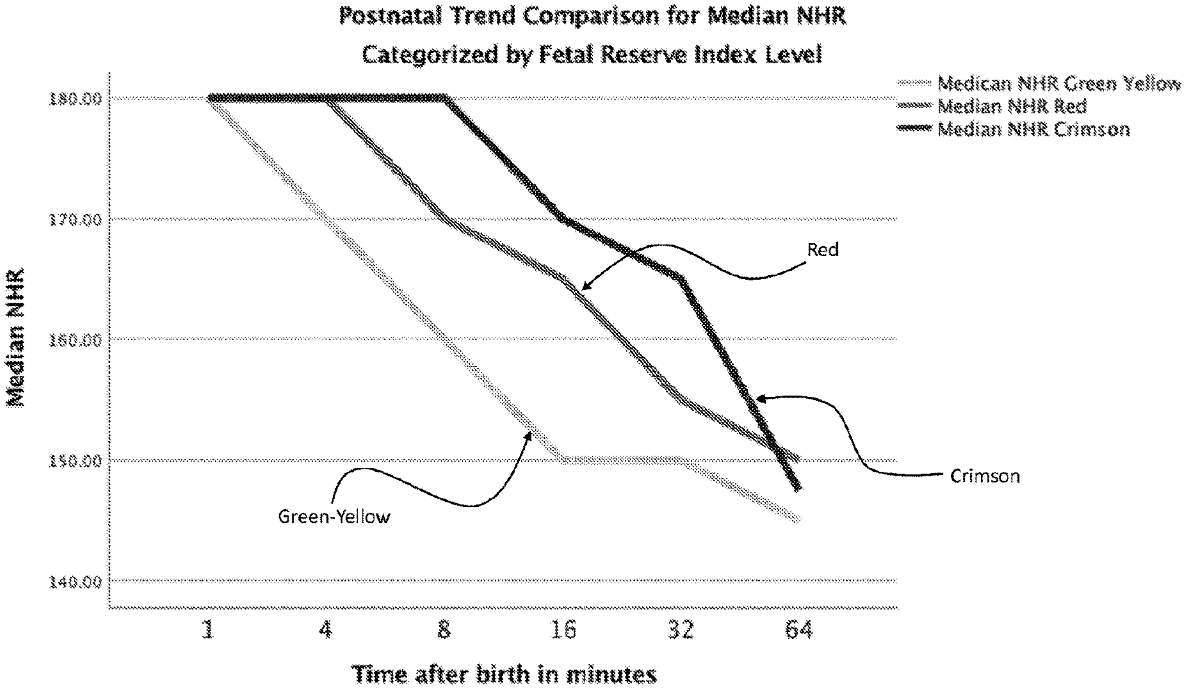
FIGS. 7 through 9 are graphs comparing the change over time for the monitored neonatal parameter of heart rate for neonates grouped according to their FRI scores.

Likewise, the NHR responses of tachycardia, delayed return to baseline, and delayed resumption of reactivity are also consistent with the above conclusion. Within the first 10 minutes following delivery, NHR for these historic data generally showed a sudden onset of marked tachycardia to over 180 and often over 200 with loss of variability and reactivity. However, there was clear discrimination in the increase in NHR and time to recovery of reactivity among the green-yellow, red and crimson cases. The higher the risk (lower FRI score), the higher the tachycardia; the lower the risk, the quicker the recovery to 160 bpm (Mantel-Cox log rank test for equality, chi square=20.02, p<0.000). By 20 min, 71% of the neonates in the green-yellow group had recovered to 160, 49% for the red group, but only 28% of the crimson group (FIG. 7). Overall, to achieve the relative safety of ≤160 bpm, the green-yellow group averaged 31 min, the red group 40 min, and the crimson group 52 min.

The pattern of $pO_2$ did not mirror that of pH or Base Excess, as $pO_2$ did increase in virtually all cases following delivery (which is consistent with oxygenation via the lungs that takes in more 02 than coming via the placenta).

Additionally, the impact of the FRI score on neonatal recovery (ordinary least squares regression) was evaluated, combining prenatal (FRI) and postnatal variables (both umbilical cord arterial blood and 4-min umbilical artery readings). More particularly, BE levels achieved by 32 min, and how long it took to recover to safe levels, were evaluated. For both blood collection times, the impact of the FRI score alone (Model 1), as well as in combination with neonatal variables (Model 2), were evaluated. In both Models 1 and 2, the FRI score explains a significant amount of variance in both the BE level achieved by 32 min, and the time it takes to recover to −12 BE (R2=0.16 and 0.14, respectively, both p<0.001).

Controlling for umbilical cord arterial blood and umbilical artery variables, the FRI score continues to make an independent contribution (beta=0.13 and 0.15, respectively, (both p<0.02) to the prediction of 32-min BE levels and to the length of the BE level recovery time to −12 BE). Umbilical cord arterial blood and umbilical artery BE also make significant, independent contributions to both of these outcomes after controlling for the effects of FRI. Model 2 explains 51% of the variance in the 32-min BE scores and 34% of the variance in recovery time. This analysis demonstrates that the combination of pre- and postnatal variables improves upon the prenatal FRI score alone as a predictor of postnatal risk of neurological injury.

pO2 as an independent variable contributes little to the explanation of either 32-min BE levels or time to recovery to −12 BE.

To determine combined predictive power for sensitivity of BE risk at 32 min, the net sensitivity of the FRI score and umbilical cord blood and umbilical artery BE, treated simultaneously, were evaluated. FRI score has a sensitivity of 83%; umbilical cord blood BE has a sensitivity of 87%. Together, they commonly identified 38 of the 53 lowest 25% BE cases at 32 min. The FRI score uniquely identified another six cases; umbilical cord blood BE correctly identified another eight cases. Hence, the net sensitivity is the sum of these jointly and uniquely identified cases, or 52/53 cases, (98%). However, the combined specificity is lowered to about 23%.

Replicating the BE analysis, the FRI score was examined with either at-birth or 4-min NHR readings, on NHR at 32 min, and recovery time to 160 bpm. The FRI score significantly influenced the prediction of both NHR levels at 32 min and recovery time.

BE and pO2 did not contribute to the prediction of either recovery time or 32-min levels.

FRI had a sensitivity of 82% for the worst 25% of NHR 32-min levels. Adding umbilical cord arterial blood BE which has a sensitivity of 86%, the two tests together jointly (both abnormal) identified 40 of the 56 (71%) worst-25% of NHR cases at 32 min. Each of the tests uniquely identified 15 more cases (combined total of 55/56 cases) (sensitivity 98%). Net specificity fell from 61 to 37%.

Table 2, below, provides the Coefficient of Determination (R-Squared) for the FRI score and neonatal parameters at 4, 8, 16, 32 and 64 minutes post-birth. In Table 2, the Base Excess parameter is the dependent variable in each case.

TABLE 2

| DEPENDENT VARIABLE IS BASE EXCESS AT EACH TIME | | | | | |
|---|---|---|---|---|---|
| PRENATAL/BIRTH | 4 | 8 | 16 | 32 | 64 |
| LAST FRI | 0.205 (<.000) | 0.255 (<.000) | 0.198 (<.000) | 0.169 (<.002) | 0.109 (<.069) |
| PO2cb | 0.097 (<.052) | 0.121 (<.009) | 0.167 (<.000) | 0.101 (<.049) | 0.059 (<.283) |
| BEcb | 0.666 (<.000) | 0.666 (<.000) | 0.701 0.000 | 0.709 (<.000) | 0.747 (<.000) |
| pHcb | 0.034 (<.557) | −0.091 (<.096) | −0.096 (<.062) | −0.187 (<.002) | −0.419 (<.000) |
| R square | 0.679 (<.000) | 0.632 (<.000) | 0.659 (<.000) | 0.540 (<.000) | 0.401 (<.000) |

Table 3, below, provides the Coefficient of Determination (R-Squared) for the FRI score and neonatal parameters at 4, 8, 16, 32, and 64 minutes post-birth. In Table 3, the pHcb (cord blood pH) parameter is the dependent variable in each case.

TABLE 3

| DEPENDENT VARIABLE IS pH AT EACH TIME | | | | | |
|---|---|---|---|---|---|
| PRENATAL/BIRTH | 4 | 8 | 16 | 32 | 64 |
| LAST FRI | 0.191 (<.024) | 0.245 (<.001) | 0.163 (<.020) | 0.032 (<.663) | −0.034 (<.641) |
| PO2cb | 0.020 (<.788) | 0.034 (<.610) | 0.006 (<.929) | −0.132 (<.063) | −0.124 (<.070) |
| BEcb | 0.009 (<.928) | −0.111 (<.185) | −0.183 (<.024) | −0.109 (<.207) | −0.313 (<.000) |
| pHcb | 0.412 (<.000) | 0.358 (<.000) | 0.458 (<.000) | 0.390 (<.000) | −0.339 (<.000) |
| R square | 0.267 (<.000) | 0.202 (<.000) | 0.191 (<.000) | 0.117 (<.000) | 0.101 (<.000) |

As the foregoing data reflect, FRI can predict with a high degree of accuracy the pattern of adaptation to extra-uterine life. Further, these data convincingly demonstrate that the FRI score taken prior to delivery of the fetus combined with one or more measurements, taken within the first minutes after birth, of, for instance, Base Excess are much better predictors of neonatal status at approximately 30 minutes after birth than the neonatal parameters by themselves.

Exemplary Methods

The discoveries herein described lend themselves to a method for reducing the risk of neurological injury to a neonatal human child, comprising the steps of:

(I) monitoring in a pregnant patient during labor at least a first set of parameters indicative of a present level of risk for neurological injury to the child as a fetus;

(II) during the period between a cervical dilatation of 10 cm in the patient and delivery of the child and/or during at least the first 5 minutes following delivery of the child, determining a present level of risk for neurological injury to the child based on the at least first set of parameters at a given point in time during labor that is between a cervical dilatation of 10 cm in the patient and delivery of the child, and wherein the determined present level of risk corresponds to one of a plurality of predetermined levels of predicted risk for neurological injury to the child as a neonate; and (III) commencing monitoring the child for one or more postnatal parameters indicative of neurological injury or its onset within the first 5 minutes following delivery of the child, and/or performing one or more measures for treating the child for neurological injury or its onset within the first 60 minutes following delivery of the child.

Stated differently and in the context of specific examples provided heretofore, the method of the present invention comprehends monitoring in the pregnant patient during labor those parameters, such as described herein, which are relevant to establishing the FRI score. Then, during the period between a cervical dilatation of 10 cm in the patient and delivery of the child and/or during at least the first 5 minutes following delivery of the child, the FRI score is determined for a given point in time during labor that is between a cervical dilatation of 10 cm in the patient and delivery of the child. Preferably, though not necessarily, that determination is made for the point in time that is just prior to delivery of the child.

The monitored parameters include, according to examples given herein. At least each of (a) FHR, (b) baseline FHR variability, (c) FHR accelerations, (d) FHR decelerations, and, optionally, (e) maternal uterine contractions. A manner of determining the present level of risk for neurological injury using these parameters has been described heretofore in connection with the FRI score.

As described heretofore, the FRI score has been discovered to correspond with statistical significance to a predetermined level of predicted risk of neurological injury to the child as a neonate. Again, in the context of the specific examples described herein, that predetermined level of predicted risk is derived from a dataset comprising historical determinations, for each of a population of children, of risk for neurological injury based on the FRI score at a given point in time during labor that is between a cervical dilatation of 10 cm in the patient and delivery of the child, correlated with data of one or more postnatal parameters of neurological injury or its onset taken from the period between delivery and for at least 30 minutes thereafter. In short, the FRI score for each child in the historical dataset corresponds to indicators of risk for neurological injury postdelivery. Using this correspondence, determination of the FRI score for a given point in time prior to delivery thus provides a statistically significant basis to predict a risk for neurological injury to the child as a neonate.

It will be understood that "historical" as used herein simply means and refers to relevant data for completed births. In the experimental examples discussed herein, those data were collected in the 1970's. However, relevant data may also include, by way of non-limiting example, contemporary data, including data generated in connection with practicing the present invention.

As those skilled in the art will appreciate, the present invention also lends itself to refinement of the predetermined risk for neurological injury as further data are generated, including through practicing the method of this invention. That is, each new circumstance or case where both prenatal and postnatal parameters are monitored permits further opportunity to evaluate the correspondence between FRI scoring and the postnatal parameters and, thus, to further refine the predetermined levels of predicted risk for neurological injury based on these additional data.

As noted, the method of the present invention comprehends that monitoring of the child for one or more postnatal parameters indicative of neurological injury or its onset is commenced within the first 5 minutes following delivery of the child, and/or that one or more measures for treating the child for neurological injury or its onset are performed within the first 60 minutes following delivery of the child. As the examples and discoveries herein given manifest, the progress of the transition from fetal to neonatal circulation proceeds much less smoothly than heretofore appreciated and, moreover, parameters indicative of a present level of risk for neurological injury to the fetus during labor correspond meaningfully with the progress of that transition. Consequently, the present invention allows caregivers to identify risks for neonatal neurologic injury far earlier in the course of labor and delivery than was heretofore possible and, therefore, to take steps which are suited to the identified risk. Those steps include, at a minimum, commencing monitoring the neonate within the first 5 minutes following delivery, so that those postnatal parameters indicative of neurological injury or its onset may be considered. Presently, such monitoring is not part of patient care. Instead, it is common that evaluation of a neonate for therapeutic measures related to neurological injury is not made until 60 minutes after birth or longer.

To the extent that the risk of neurological injury is deemed significant enough to warrant intervention (which determination may be based on conventional criteria), the physician or other caregiver can take steps necessary to eliminate or reduce the likelihood that neurological injury will actually ensue. Such intervention may include at least one of the following measures: intubating and/or oxygenating the neonate upon delivery and prior to clamping and cutting of the umbilical cord; intubating and/or oxygenating the neonate after the umbilical cord is clamped and cut; performing brain cooling; and/or other therapeutic measures known to those skilled in the art. Again, the present invention improves upon the prior art in these regards by identifying the risk far earlier in labor and delivery and, thus, ensuring that monitoring is undertaken rapidly following delivery so that intervention may likewise be undertaken sooner, rather than later, as needed.

As described elsewhere herein, the method of this invention may further comprehend the step of assigning one or plurality of predefined risk categories (e.g., “green,” “red,” “crimson”) to the child based on the determined present level of risk. As discussed, the assigned category further corresponds to one of the predetermined levels of predicted risk for neurological injury to the neonate. For instance, the “crimson” group or category represents the most significant level of predicted risk. Of course, it will be understood that the number and designations (e.g., “green,” “red,” “crimson”) for the categories are exemplary and not intended to be limiting.

As also discussed elsewhere herein, the plurality of predetermined levels of predicted risk may comprise predicted Base Excess values at approximately 30 minutes post-delivery. Again in the context of specific examples provided herein, the FRI score proximate delivery has been found to constitute a statistically significant predictor of Base Excess at approximately 30 minutes post-delivery, such that establishment of the FRI score near the time of delivery provides a meaningful prediction of the neonate’s future Base Excess and, hence, the FRI score serves to guide monitoring and treatment post-delivery so as to eliminate or mitigate risks of neurological injury.

In a variant of the foregoing method, there is comprehended a further step (IV) of identifying a potential risk for neurological injury to the child based on the one or more postnatal parameters (e.g., neonatal blood pH, Base Excess, neonatal heart rate (NHR), and $pO_2$) as monitored within the first 5 minutes following delivery of the child, wherein the one or more postnatal parameters as monitored within the first 5 minutes following delivery of the child correspond to one of the predetermined levels of predicted risk for neurological injury to the child as a neonate.

Stated differently and in the context of the examples provided heretofore, the method of the present invention comprehends monitoring in the neonate those parameters, such as described herein, which are indicative of neurological injury or its onset. Then, within the first 5 minutes following delivery of the child, a predetermined level of predicted risk for neurological injury to the child at a future point in time following delivery is determined based on the pre-established correspondence between monitored neonatal parameters within the first 5 minutes following delivery and at a point in time thereafter; e.g., approximately 30 minutes following delivery.

Again, in the context of the examples described herein, that predetermined level of predicted risk is derived from a dataset comprising historical determinations, for each of a population of children, of risk for neurological injury based on at least the monitored neonatal parameters within the first 60 minutes following delivery. Using the determined correspondence between these monitored parameters at different points in time following delivery, determination of values for one or more of these neonatal parameters during the first 5 minutes following delivery thus provides a statistically significant basis to predict a risk for neurological injury to the neonatal child at a future time following delivery.

Again, those skilled in the art will appreciate that the present invention also lends itself to refinement of the predetermined risk for neurological injury as further data are generated, including through practicing the method of this invention. That is, each new circumstance or case where postnatal parameters are monitored permits further opportunity to evaluate the correspondence between values for the postnatal parameters at various times following delivery and, thus, to further refine the predetermined risk for neurological injury based on these additional data.

As set forth in the experimental data above, the sensitivity of using both the FRI score and the one or more neonatal parameters to determine a level of risk at, for instance, 30 minutes post-delivery is superior to using either parameter by itself. Consequently, the additional step (IV) of the present invention provides a variant in which the level of risk at X-minutes following delivery may be established with greater certainty than could be obtained using FRI or the monitored neonatal parameters to the exclusion of the other. According to this form of the invention, it will be appreciated that the historical data on which a predetermined risk of neurological injury to the neonate is based will comprehend evaluation of the correspondence between, on the one hand, each of the FRI score and the value of the one or more monitored neonatal parameters within 5 minutes of delivery and, on the other hand, the value of the one or more monitored neonatal parameters at a time following delivery that is later than 5 minutes (e.g., approximately 30 minutes).

Exemplary Apparatus

Figure 16:
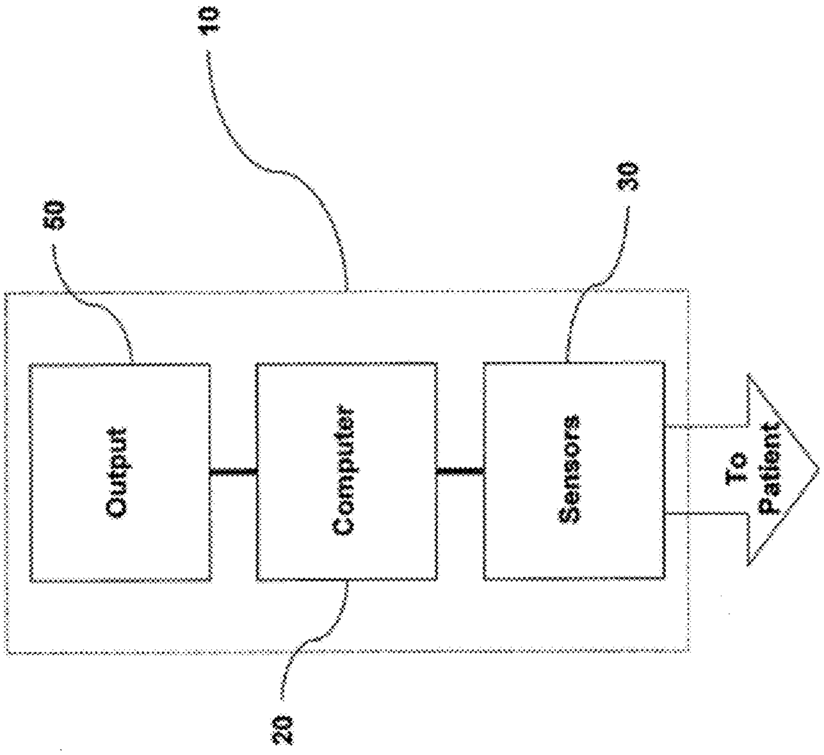
FIG. 16 is a diagrammatic depiction of an exemplary construction for an apparatus according to the present invention.

According to one embodiment, shown in FIG. 16, an apparatus 10 for implementing the methods herein described comprises at least one computer 20 operative to: receive during labor, such as from one or more sensors 30 connected to a patient 40, input signals corresponding to at least a first set of parameters indicative of a present level of risk for neurological injury to the child as a fetus; receive from the neonatal child input signals corresponding to one or more postnatal parameters indicative of neurological injury or its onset; and determine, during the period between a cervical dilatation of 10 cm in the patient and delivery of the child and/or during at least the first 5 minutes following delivery of the child, a present level of risk for neurological injury to the child based on the at least first set of parameters at a given point in time during labor that is between a cervical dilatation of 10 cm in the patient and delivery of the child, wherein the determined level of risk corresponds to one of plurality of predetermined levels of predicted risk for neurological injury to the child as a neonate. At least one output 50 is operatively connected to the at least one computer. The at least one computer is further operative to indicate via the at least one output within the first 5 minutes following delivery of the child: the determined level of risk and/or the corresponding one of the plurality of predetermined levels of predicted risk for neurological injury to the child as a neonate; and information representing the received input signals corresponding to the one or more postnatal parameters.

Respecting the first set of parameters, the at least one computer 20 is, per an exemplary embodiment, operative to determine from the input of FHR each of baseline FHR variability, FHR accelerations, and FHR decelerations, to determine when any one or more of at least (a) FHR, (b) baseline FHR variability, (c) FHR accelerations, and (d) FHR decelerations each exhibit at least one non-reassuring characteristic (for instance, the computer may be programmed with the characteristics of non-reassurance for the aforementioned parameters, such as set forth in herein, and is operative to compare those characteristics with the input signals and determine baseline FHR variability, FHR accelerations, and FHR decelerations data), and, further, to determine a level of risk of neurological injury corresponding to the number of the parameters (a) through (d) that are simultaneously, independently non-reassuring, such as according to the scheme heretofore described. This may be accomplished, for example, by the implementation of a simple algorithm which carries out the FRI scoring methodology as heretofore described.

Per another embodiment, the additional parameter of (e) maternal uterine activity may be monitored and included in the determination of the level of risk. Further to this embodiment, the input signals further comprise input signals indicative of maternal uterine activity and the at least one computer 20 is operative to determine the parameters (a) through (e) based on the FHR and maternal uterine activity input signals, and to determine whether each parameter (a) through (e) exhibits at least one non-reassuring characteristic (again, for instance, the at least one computer may be programmed with the characteristics of non-reassurance for the aforementioned parameters (a) through (e), such as set forth in herein, and is operative to compare those characteristics with the input signals). The at least one computer is further operative to transform the number of the parameters (a) through (e) that simultaneously exhibit at least one non-reassuring characteristic into an indication of the present level of risk to the child risk to the child for neurological injury corresponding to the number of the parameters (a) through (e) that simultaneously, independently exhibit at least one non-reassuring characteristic. This may be accomplished, as already noted, by the implementation of a simple algorithm which carries out the FRI scoring methodology as heretofore described.

Operative connection of these various elements 20, 30, and 50, which may be accomplished by any known means, is indicated by bold lines. The at least one output 50 may comprise, for example, a video display and/or a printer, warning lights (such as, for instance, a plurality of score-specific lights each corresponding to a different level of risk), an audible alarm, etc. It is also contemplated that the apparatus may, alternatively or in addition, be operative to provide other information, including FHR tracings, uterine activity tracings, and/or further information related to the level of risk presently indicated for the fetus, including, by way of non-limiting example, instructions to the clinician or clinicians pertaining to a predetermined action required or recommended for the identified level of risk. Such other information may be provided through the at least one output 50, for example. The output may, optionally, take the form of the display described in Published U.S. Application 2019/0274618, modified according to the present disclosure to also display the determined present level of risk to the neonate for neurological injury.

Figure 17:
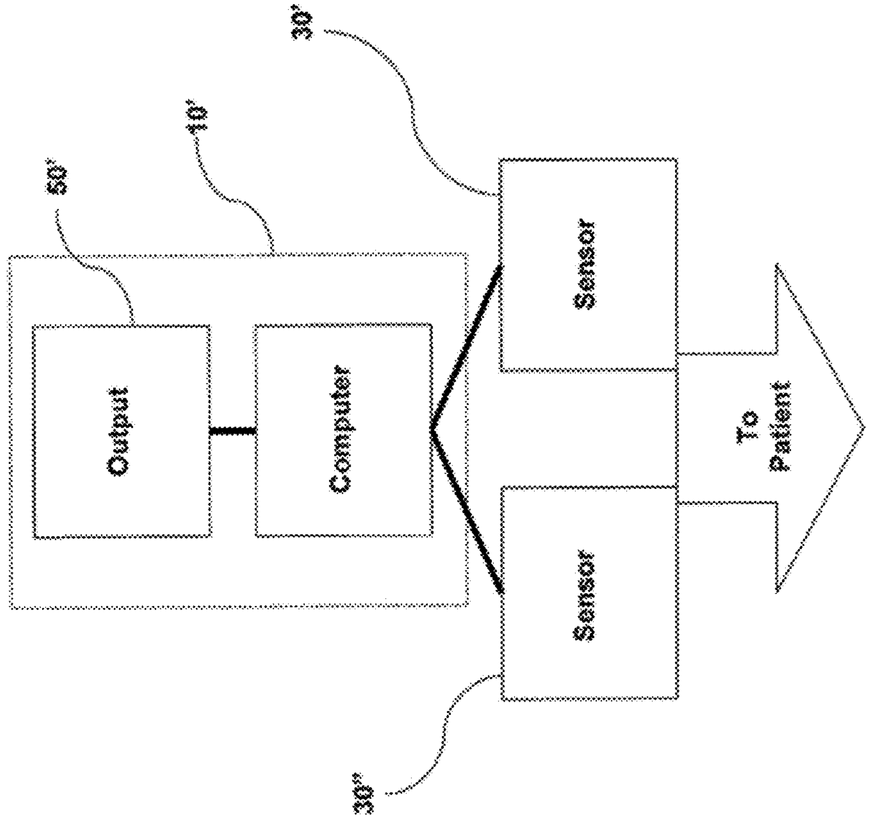
FIG. 17 is a diagrammatic depiction of a second exemplary construction for an apparatus according to the present invention.

It is contemplated that the apparatus 10 may comprise a self-contained unit comprising the one or more sensors 30 capable of monitoring/receiving user-inputs indicative of the aforementioned parameters, such as shown diagrammatically in FIG. 16, or a separate unit 10' which receives inputs corresponding to these parameters from other, separate sensors 30', 30" (FIG. 17). If the former (FIG. 16), the at least one output 50 may, as noted, further be able to provide outputs including one or more of a display and/or printout showing FHR and maternal uterine contraction tracings, such as would be provided with conventional FHM and uterine contraction sensors. If the latter (FIG. 17), the apparatus may be a separate apparatus connectable to a FHM device and uterine contraction sensor (each providing their own tracings) and capable of receiving data therefrom.

Figure 18:
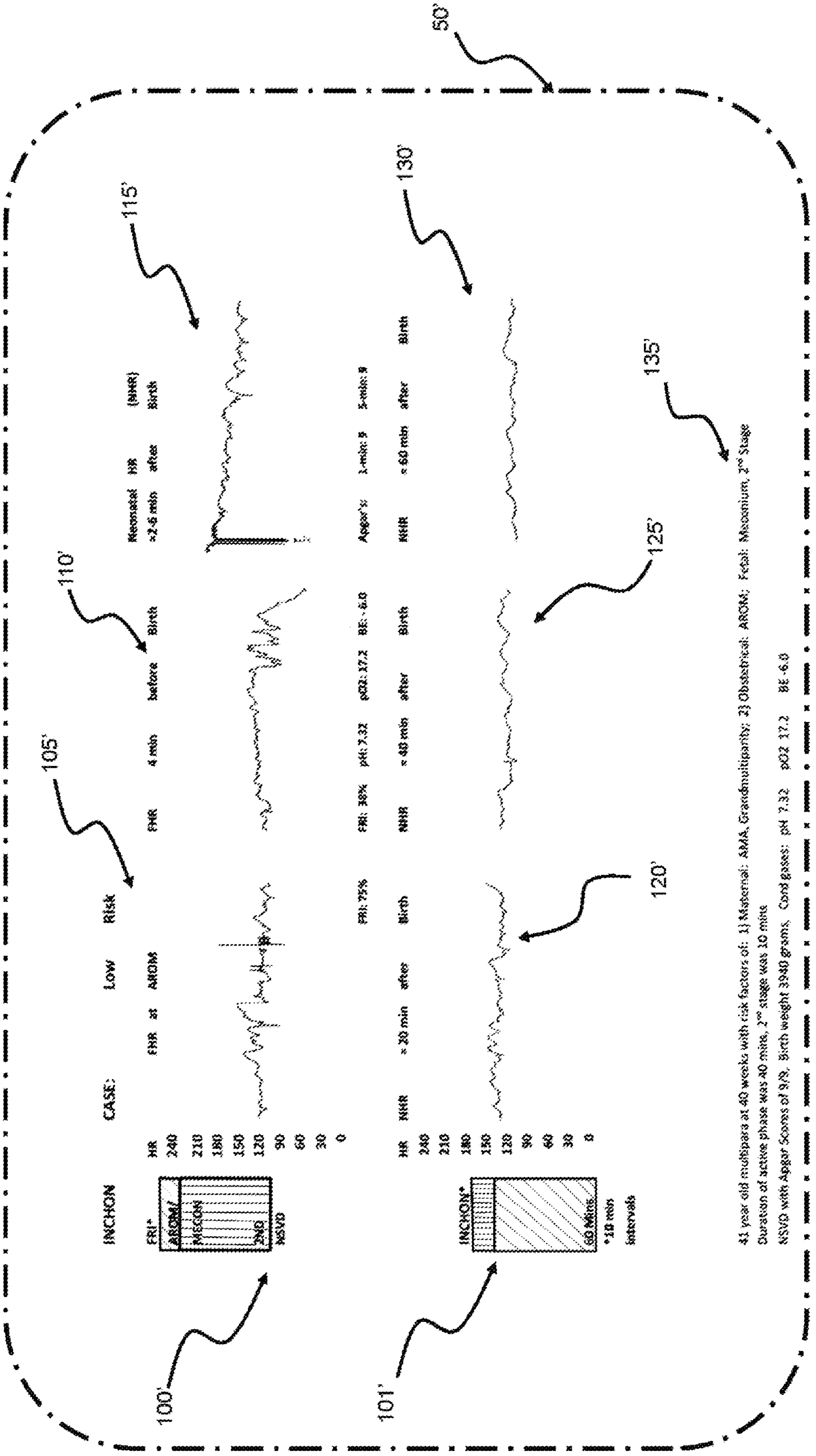
FIG. 18 is a first exemplary embodiment of an output display according to the present invention.
Figure 19:
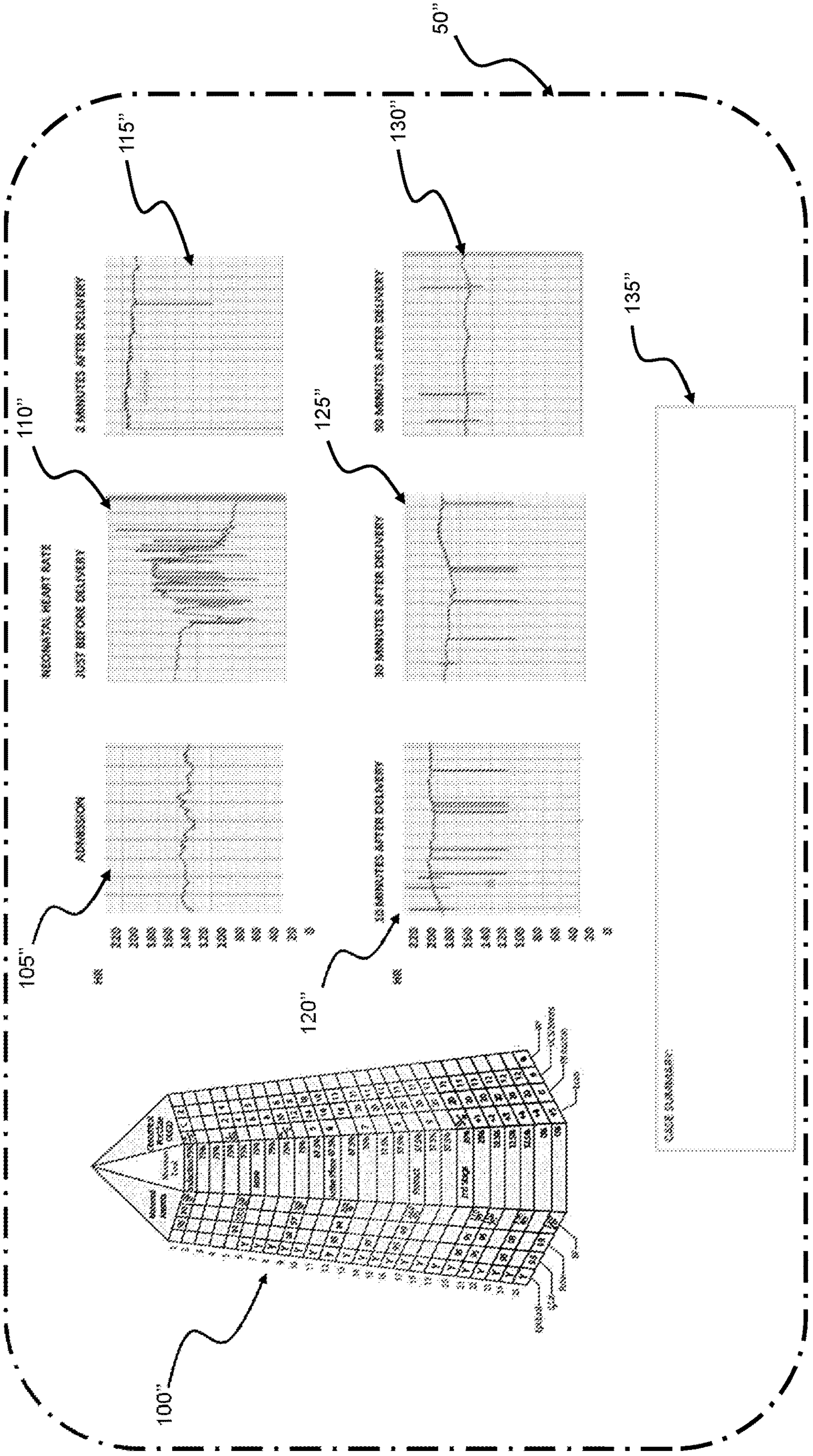
FIG. 19 is a second exemplary embodiment of an output display according to the present invention.

With reference being had to FIGS. 18 and 19, there are shown embodiments of the present invention wherein the output provides in a single output display a plurality of data relevant to labor and delivery and the level of risk of neurological injury to the fetus and/or neonate.

In each of the examples of FIGS. 18 and 19, the at least one computer is operative, in the manner heretofore described, to determine at predetermined points in time during labor a present level of risk to the fetus based on the first set of parameters, as well as to receive input signals corresponding to the heart rate of the neonatal child (NHR). The at least one output associated with the at least one computer comprises a monitor which depicts in a single visual display each of: (i) indicia for indicating the determined present level of risk to the fetus during labor and signaling the need for possible intervention in labor; (ii) information respecting the FHR at a plurality of discrete periods of time and NHR at a plurality of discrete periods of time preceding delivery of the child; and (iii) information respecting the NHR at a plurality of discrete periods of time following delivery of the child.

In FIG. 18, an embodiment is shown wherein the output 50' depicts information respecting each of the FHR at a plurality of discrete periods of time prior to delivery of the child, as well as the NHR at a plurality of discrete periods of time following delivery of the child. As shown in FIG. 18, this NHR information in the illustrated embodiment constitutes extracts of FHR and NHR tracings for each of a plurality of discrete periods before, and following, delivery; namely, FHR at the point of artificial rupture of the membrane (AROM) 105', FHR 4 minutes prior to delivery of the child 110', NHR at 2-6 minutes following delivery 115', NHR at 20 minutes following delivery 120', NHR at 40 minutes following delivery 125', and NHR at 60 minutes following delivery 130'. Each extract of a tracing, whether FHR or NHR, comprehends a predefined increment—e.g., 40 seconds—around the specific, discrete period of time captured. For example, the tracing extract shown for the discrete period of time designated "4 minutes prior to delivery" (110') would include the FHR tracing at that discrete period of time, as well as the tracing for the 20 seconds prior to, and the 20 seconds after, that time.

As shown in the exemplary embodiment of FIG. 18, it is also contemplated that the display may include additional information relevant to any one or more of the FHR and NHR tracings 105' through 130'. For example, it is shown in the illustrated embodiment that the FHR tracings 105' and 110' each have provided proximate thereto the FRI score at the corresponding time of the tracing. Also provided are cord gas data for pH, $pO_2$ and BE proximate the FHR tracing 110'. Similarly, the NHR tracing 115' includes Apgar scores at 1 minute and 5 minutes after delivery.

Also depicted in the display 50' of FIG. 18 are indicia 100', 101' for indicating the determined present level of risk to the fetus during labor and signaling the need for possible intervention in labor. This indicia, per the illustrated embodiment, comprehend a graphical representation of the FRI score calculated in the manner heretofore described. More specifically, the indicia 100', 101' comprise color-coded bars depicting representing assigned categories of risk as heretofore described. The indicia 100' and 101' are also characterized in the illustrated embodiment as depicting the FRI score calculated in a number of equivalent increments of time. More specifically, each of the indicia 100' and 101' show a plurality of sequential FRI scores calculated at 10-minute increments over a continuous period of time. In the case of indicia 100', the total period of time comprehends the period of time over which the FHR and NHR tracings 105', 110', and 115' are provided; the indicia 101' comprehend the period of time over which the NHR tracings 120', 125' and 130' are provided. As will be appreciated, this correspondence permits the correlation of relevant FRI scores and NHR/FHR data.

The indicia 100' and 101' may also include, as shown in the embodiment of FIG. 18, information respecting key events or other relevant data respecting the FRI score and/or the progress of labor and delivery. For instance, the indicia 100' include text identifying AROM, meconium passage (MECON), onset of the $2^{nd}$ stage of labor ($2^{ND}$) and delivery (in this instance, identified as normal, spontaneous vaginal delivery, or NSVD).

It will be appreciated that the indicia 100' and 101' of the embodiment of FIG. 18 will not necessarily depict the FRI scores over the entire course of labor and delivery. Rather, in the embodiment of FIG. 18, the FRI scores of indicia 100' and 101' comprehend periods of time relevant to the information shown in the FHR and NHR tracings of 110' through 105'.

Of course, it will be understood that the foregoing information and indicia would be visible on the display as, or at least after, it occurs. Thus, the FHR tracing designated "4 minutes prior to delivery" (110') would not be populated on the display 50' until its occurrence during labor.

Furthermore, it is contemplated by the present invention that the display 50' includes an area 135' for a "Case Summary" providing an overview of the depicted information, as well as any other potentially relevant data or other considerations. This summary could be populated by a user (e.g., a physician or other health care professional). When the output is in the form of a computer display, the "Case Summary" could be input via keyboard of other manual entry means. When the output is in the form of a physical document, it is also contemplated that the "Case Summary" could be a box or other blank area to be filled in by hand. In the embodiment of FIG. 18, the exemplary "Case Summary" text reads as follows:

> 41 year old multipara at 40 weeks with risk factors of: 1) Maternal: AMA, Grandmultiparity; 2) Obstetrical: AROM; Fetal: Meconium, 2nd Stage Duration of active phase was 40 mins, 2nd stage was 10 mins NSVD with Apgar Scores of 9/9, Birth weight 3940 grams, Cord gases: pH 7.32 $pO_2$ 17.2 BE −6.0

Turning next to FIG. 19, there is shown a second embodiment of an output display. According to this embodiment, the first set of concurrent clinical parameters comprise (a) FHR, (b) baseline FHR variability, (c) FHR accelerations, and (d) FHR decelerations. As described above, the at least one computer receives the input signals corresponding to FHR. The at least one computer is operative to determine the parameters (b) through (d) based on the FHR input signals. Per this embodiment, the at least one computer is further operative to determine at predetermined points in time during labor a present level of risk to the fetus based on the first set of concurrent clinical parameters. The output 50" depicts in a single graphical user interface 100': (i) information respecting one or more of the first set of concurrent clinical parameters (a) through (d) over time during labor, and the appearance of which single graphical user interface includes indicia for indicating the determined present level of risk to the fetus at any given point in time during labor and signaling the need for possible intervention in labor. This graphical user interface is depicted as the obelisk 100" of FIG. 19.

Pursuant to the instant invention, the apparatus is further characterized in that the at least one computer is further operative to receive input signals corresponding to the heart rate of the neonatal child (NHR).

Moreover, the output 50" depicts information respecting each of the FHR at a plurality of discrete periods of time prior to delivery of the child, as well as the NHR at a plurality of discrete periods of time following delivery of the child. As shown in FIG. 19, this NHR information in the illustrated embodiment constitutes extracts of FHR and NHR tracings for each of a plurality of discrete periods before, and following, delivery; namely, FHR at admission of the mother to the hospital 105", FHR just prior to delivery of the child 110", NHR at 2 minutes following delivery 115", NHR at 10 minutes following delivery 120", NHR at 30 minutes following delivery 125", and NHR at 50 minutes following delivery 130". Each extract of a tracing, whether FHR or NHR, comprehends a predefined increment—e.g., 40 seconds—around the specific, discrete period of time captured. For example, the tracing extract shown for the discrete period of time designated "just prior to delivery" (110") would include the FHR tracing at that discrete period of time, as well as the tracing for the 20 seconds prior to, and the 20 seconds after, that time.

As with the first embodiment, it will be understood that the foregoing information and indicia would be visible on the display as, or at least after, it occurs. At least according to this embodiment, it would thereafter persist in the display 50". Similarly, the FRI score information (shown at 100" and 101") could be shown as it becomes available during the course of labor. At the conclusion of labor and delivery, specific excerpts (such as the tracings shown) could then be specifically populated in the single output display, including according to parameters defined by the user.

Finally, it is contemplated by the present invention that the display 50" includes an area 135" for a "Case Summary" providing an overview of the depicted information, as well as any other potentially relevant data or other considerations. This summary could be populated by a user (e.g., a physician or other health care professional). When the output is in the form of a computer display, the "Case Summary" could be input via keyboard of other manual entry means. When the output is in the form of a physical document, it is also contemplated that the "Case Summary" could be a box or other blank area to be filled in by hand.

It will be appreciated that the output displays of the foregoing embodiments may, in the first instance, take the form of a computer display (e.g., a monitor). However, these displays may also, or alternatively, take the form of a of a physical document (e.g., a hard-copy printout, etc.).

By the foregoing, it will be appreciated that the present invention provides a means for reducing the risk of neurological injury to the neonate.

The embodiments are shown and described in order to explain the principles of the innovation and its practical application to enable one skilled in the art to utilize the innovation in various embodiments and with various modifications as are suited to the particular use contemplated. Although only a few embodiments of the present innovations have been described in detail in this disclosure, those skilled in the art who review this disclosure will readily appreciate that many modifications are possible without materially departing from the novel teachings and advantages of the subject matter recited. Accordingly, all such modifications are intended to be included within the scope of the present innovations. Other substitutions, modifications, changes and omissions may be made in the design, operating conditions and arrangement of the exemplary embodiments without departing from the spirit of the present innovations.

The invention in which an exclusive property or privilege is claimed is defined as follows:

1. An apparatus for reducing the risk of neurological injury to a neonatal human child, comprising:

at least one computer operative to:

receive from a monitored patient during labor input signals corresponding to at least a first set of parameters indicative of a present level of risk for neurological injury to the child as a fetus;

receive from the neonatal child input signals corresponding to one or more postnatal parameters indicative of neurological injury or its onset;

determine, prior to delivery of the child and/or during at least the first 5 minutes following delivery of the child, a present level of risk for neurological injury to the child based on the at least first set of parameters at a given point in time during labor that is just prior to delivery of the child, wherein the determined level of risk corresponds to one of a plurality of predetermined levels of predicted risk for neurological injury to the child as a neonate;

at least one output operatively connected to the at least one computer, wherein the at least one computer is further operative to indicate via the at least one output by no later than the first 5 minutes following delivery of the child:

the determined level of risk and/or the corresponding one of the plurality of predetermined levels of predicted risk for neurological injury to the child as a neonate; and information representing the received input signals corresponding to the one or more postnatal parameters;

wherein the first set of parameters comprise (a) FHR, (b) baseline FHR variability, (c) FHR accelerations, and (d) FHR decelerations, wherein the input signals comprise at least FHR;

wherein the input signals further comprise input signals indicative of maternal uterine activity, wherein the first set of parameters further comprise (e) maternal uterine activity;

wherein the at least one computer is further operative to receive user-inputs indicative of the presence in the patient of one or more (f) maternal risk factors, (g) obstetrical risk factors, and (h) fetal risk factors which elevate the level of fetal risk during labor;

wherein the at least one computer is operative to determine the parameters (a) through (e) based on the FHR and maternal uterine activity input signals, and wherein the determination of the present level of risk to the child for neurological injury takes into account the monitored parameters of at least (a) through (e) that exhibit, at a given point in time during labor that is just prior to delivery of the child, at least one non-reassuring characteristic from a plurality of pre-defined non-reassuring characteristics and the total number present of the (f) maternal risk factors, (g) obstetrical risk factors, and (h) fetal risk factors which elevate the level of fetal risk during labor;

wherein the plurality of predetermined levels of predicted risk for neurological injury to the child as a neonate comprise predicted Base Excess and/or pH values for 30 minutes post-delivery.

2. The apparatus of claim 1, wherein the determination of the present level of risk to the child for neurological injury comprises determining whether each parameter (a) through (e) exhibits at least one of the non-reassuring characteristics at the given point in time during labor that is just prior to delivery of the child, and transforming the number of the parameters (a) through (e) that simultaneously exhibit at least one of the non-reassuring characteristics and the total number of the parameters (f) through (h) which are present into an indication of the present level of risk to the child for neurological injury corresponding to the number of the parameters (a) through (e) that simultaneously, independently exhibit at least one non-reassuring characteristic and the total number present of the (f) maternal risk factors, (g) obstetrical risk factors, and (h) fetal risk factors which elevate the level of fetal risk during labor.

3. The apparatus of claim 2, wherein the at least one computer is further operative to assign one of a plurality of predefined risk categories to the child based on the determined present level of risk.

4. The apparatus of claim 3, wherein the predefined risk categories comprise three risk categories, the determined present level of risk falls into one of the three risk categories, and the assigned category of risk corresponds to one of the plurality of predetermined levels of predicted risk for neurological injury to the child as a neonate.

5. The apparatus of claim 1, wherein the at least one computer is further operative to assign one of a plurality of predefined risk categories to the child based on the determined present level of risk.

6. The apparatus of claim 5, wherein the predefined risk categories comprise three risk categories, the determined present level of risk falls into one of the three risk categories, and the assigned category of risk corresponds to one of the plurality of predetermined levels of predicted risk for neurological injury to the child as a neonate.

7. The apparatus of claim 1, wherein the one or more postnatal parameters indicative of neurological injury or its onset are selected from among the group of neonatal blood pH, Base Excess, neonatal heart rate (NHR), and $pO_2$.

8. The apparatus of claim 1, wherein the plurality of predetermined levels of predicted risk for neurological injury to the child as a neonate are derived from a dataset comprising historical determinations of risk for neurological injury based on the at least first set of parameters at a given point in time during labor that is between a cervical dilatation of 10 cm in the patient and delivery of the child, correlated with historical data of one or more postnatal parameters indicative of neurological injury or its onset taken from the period between delivery and for at least the first 30 minutes thereafter.

* * * * *